(12) United States Patent
Schulze et al.

(10) Patent No.: US 7,988,691 B2
(45) Date of Patent: Aug. 2, 2011

(54) ORTHOPAEDIC TRAUMA BONE PLATE KIT

(75) Inventors: Dale R. Schulze, Ft Wayne, IN (US); Jack F. Long, Warsaw, IN (US); Priya R. Prasad, Sunrise, FL (US); Marc E. Ruhling, Goshen, IN (US)

(73) Assignee: DePuy Products, Inc., Warsaw, IN (US)

( * ) Notice: Subject to any disclaimer, the term of this patent is extended or adjusted under 35 U.S.C. 154(b) by 759 days.

(21) Appl. No.: 11/707,459

(22) Filed: Feb. 13, 2007

(65) Prior Publication Data

US 2008/0234676 A1 Sep. 25, 2008

(51) Int. Cl.
*A61B 17/70* (2006.01)
*A61B 17/58* (2006.01)

(52) U.S. Cl. ........................................................ 606/71
(58) Field of Classification Search ............... 606/54, 606/60, 61, 69, 70, 71, 280–299
See application file for complete search history.

(56) References Cited

U.S. PATENT DOCUMENTS

| | | | |
|---|---|---|---|
| 2,406,832 A | 9/1946 | Hardinge | |
| 3,842,825 A | 10/1974 | Wagner | |
| 4,289,123 A * | 9/1981 | Dunn | 606/250 |
| 4,573,454 A | 3/1986 | Hoffman | |
| 5,364,398 A | 11/1994 | Chapman et al. | |
| 5,462,547 A | 10/1995 | Weigum | |
| 5,496,371 A * | 3/1996 | Eppley et al. | 623/17.18 |
| 5,527,310 A | 6/1996 | Cole et al. | |
| 5,531,747 A * | 7/1996 | Ray | 606/278 |
| 5,558,674 A | 9/1996 | Heggeness et al. | |
| 5,702,395 A * | 12/1997 | Hopf | 606/250 |
| 5,704,936 A * | 1/1998 | Mazel | 606/254 |
| 5,766,175 A | 6/1998 | Martinotti | |
| 5,776,201 A * | 7/1998 | Colleran et al. | 623/20.15 |
| 5,800,162 A | 9/1998 | Shimodaira et al. | |
| 5,879,352 A * | 3/1999 | Filoso et al. | 606/62 |
| 5,975,904 A | 11/1999 | Spiegel | |
| 5,993,449 A * | 11/1999 | Schlapfer et al. | 606/60 |
| 6,136,002 A * | 10/2000 | Shih et al. | 606/250 |
| 6,340,362 B1 | 1/2002 | Pierer et al. | |
| 6,524,315 B1 | 2/2003 | Selvitelli et al. | |
| 6,602,256 B1 * | 8/2003 | Hayes | 606/296 |
| 6,616,669 B2 * | 9/2003 | Ogilvie et al. | 606/279 |
| 6,755,839 B2 * | 6/2004 | Van Hoeck et al. | 606/87 |
| 6,991,632 B2 * | 1/2006 | Ritland | 606/258 |

(Continued)

FOREIGN PATENT DOCUMENTS

EP 1905368 4/2008

(Continued)

OTHER PUBLICATIONS

European Search Report for EP 08 25 0482, dated Jun. 20, 2008 (3 pages).

*Primary Examiner* — Thomas C Barrett
*Assistant Examiner* — Christopher Beccia

(57) ABSTRACT

A kit for the construction of a bone plate assembly for fixation of a fractured bone is provided. The kit includes a plurality of plate members, a connecting member for retaining the plurality of plate members in a desired configuration and a plurality of locking members for securing the plate members to the connecting member.

17 Claims, 21 Drawing Sheets

U.S. PATENT DOCUMENTS

| | | | |
|---|---|---|---|
| 7,186,256 B2 * | 3/2007 | Michelson | 606/71 |
| 7,344,537 B1 * | 3/2008 | Mueller | 606/278 |
| 2002/0128653 A1 | 9/2002 | Haidukewych | |
| 2004/0102778 A1 * | 5/2004 | Huebner et al. | 606/71 |
| 2006/0079892 A1 | 4/2006 | Roychowdhury et al. | |
| 2006/0235405 A1 * | 10/2006 | Hawkes | 606/69 |
| 2007/0293863 A1 * | 12/2007 | Reimels et al. | 606/69 |
| 2008/0108998 A1 * | 5/2008 | Lindemann | 606/71 |

FOREIGN PATENT DOCUMENTS

| | | |
|---|---|---|
| WO | 2005117731 | 12/2005 |
| WO | WO2006/050400 | 5/2006 |
| WO | 2006116853 | 11/2006 |

* cited by examiner

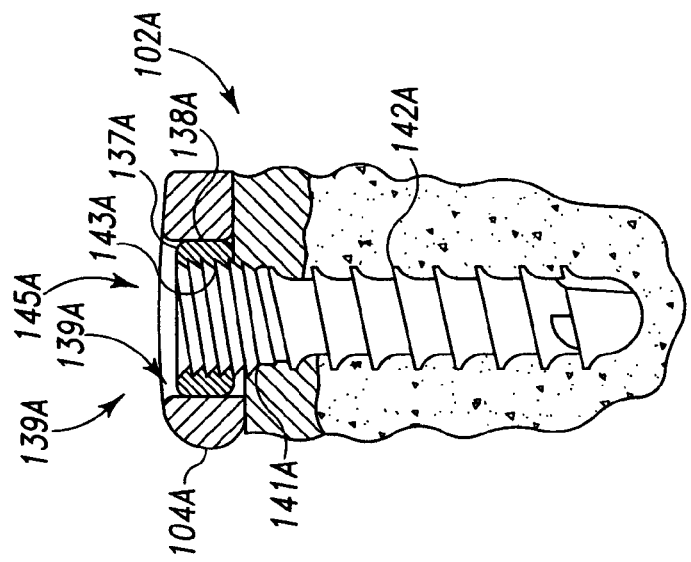
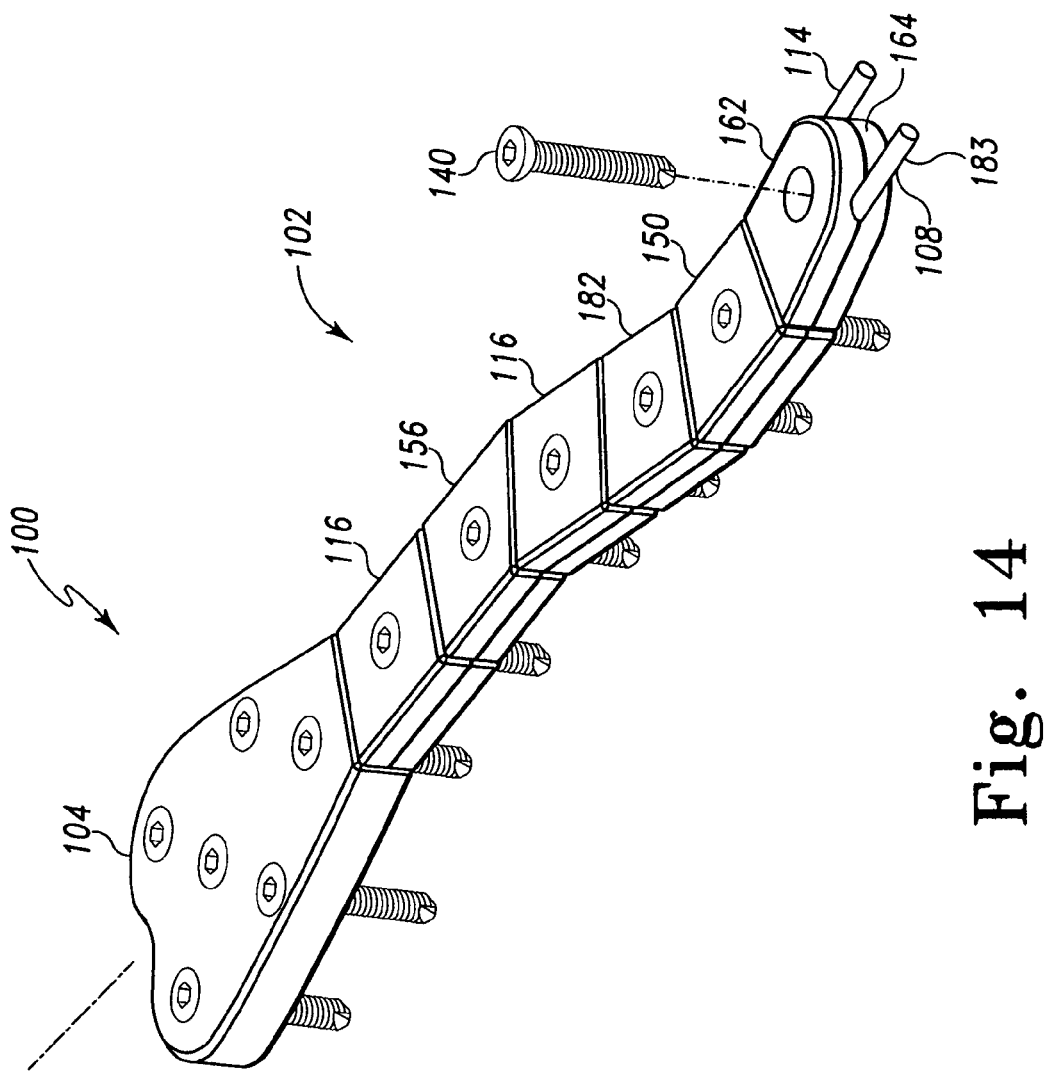
Fig. 14A
Fig. 14

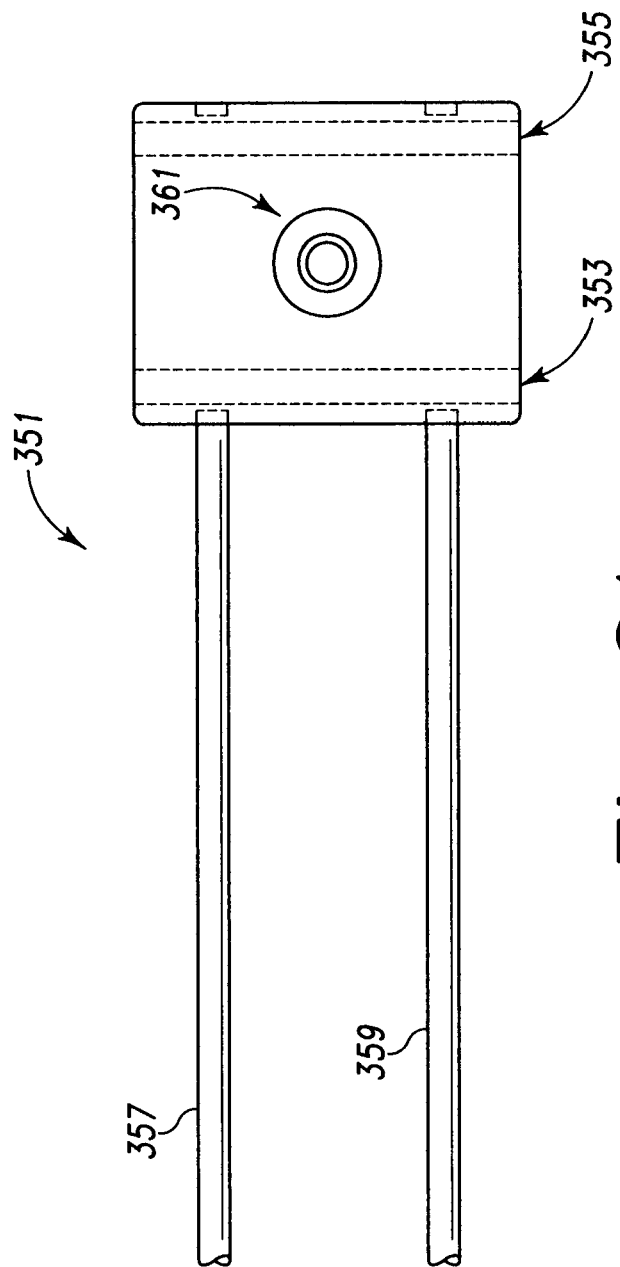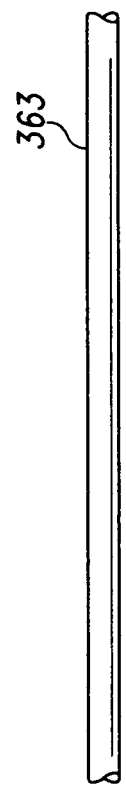
Fig. 24
Fig. 24A

ORTHOPAEDIC TRAUMA BONE PLATE KIT

FIELD

This application relates generally to the field of orthopedics, and more specifically to bone plates and systems for stabilization and compression of fractured or otherwise damaged bones. This application is related to U.S. patent application Ser. No. 11/527,951, filed Sep. 27, 2006 and titled "Flexible Bone Fixation Device", and which is hereby incorporated herein by reference in its entirety.

BACKGROUND

Bone plates for internal fixation of fractured bones should generally conform to the contours of the fractured bone surface. This is especially true for compression plates that are screwed tightly against the bone. Matching the plate shape to the bone contours is important with compression plates in order to allow proper distribution of loads between the bone and the plate during healing of the fracture. It is also desirable for the plate to have a low profile and to blend with the bone surface as much as possible so as not to irritate or interfere with surrounding soft tissues, nerves, tendons, vessels, etc.

One type of bone plate for acetabular and other pelvic fractures is called a reconstruction bar. Conventional reconstruction bars are generally formed from a biocompatible metal that may be bent by the surgeon using special tools in order to configure the bar to conform to the bone. Typically the surgeon first forms a thin metal template by hand to conform to the bone surface at the fracture site. Working through an open incision, the surgeon bends the template to approximate the desired shape, places the template against the bone surface, removes the template, adjusts the shape of the template and repeats these steps until the template closely matches the shape of the bone surface. Then the surgeon, sometimes with the help of an assistant, uses a number of special forming tools to bend the reconstruction bar to be implanted into approximately the same configuration as the template, visually holding the bar and template side-by-side to assess when the bar is adequately similar to the template. This procedure may take several minutes of time and a significant amount of skill. The bar may then be attached to the bone using conventional cortical screws. It is not likely that the bar shape exactly matches the bone surface shape, so tightening of the bone screws may draw the bar against the bone surface, thereby inducing bending preloads at various locations along the bar due to the spring-back characteristic of the bar material. Alternatively, the bar may be implanted with significant gaps between various locations of the bar and the bone surface, resulting in the uneven transfer of loads between the bone and bar construct. Therefore, it would be advantageous to provide a reconstruction bar that may be implanted more quickly by the surgeon, requires fewer ancillary tools, is more conformable and contoured to the bone surface and is at least as effective as a fixation device compared to conventional reconstruction bars.

Another issue currently faced by orthopedic device manufacturers is the need to provide a full line of bone plates for a large variety of bone fractures and patient anatomies. The manufacturing costs associated with forming each rigid, one-piece bone plate is significant due largely to the need to configure the plate to approximately match the bone surface shape. Furthermore, a large product inventory must be provided to the user (hospitals) to be prepared for the many types of fractures and patient anatomies to be treated. Accordingly, it would be advantageous to provide bone plates that have broader indications, where each plate may be suitable for a larger variety of fractures and patient anatomies than currently available plates. Potentially, such bone plates may be produced at lower costs than current plates and inventories reduced without compromising surgical outcomes.

What is also needed is a bone fixation device and method such as described above (may be implanted quickly, requires fewer ancillary tools, is at least as effective as a fixation device compared to conventional fixation devices) that may be configured to conform to a broad, contoured bone surface. The fixation device may, for example, reduce the need to use multiple bone plates for particular types of fractures, including comminuted acetabular fractures (see Chapter 20 of Orthopaedic Surgery Essentials: TRAUMA, published by Lippincott Williams and Wilkins, 2006).

There is also a need to provide surgeons with devices and methods to create custom, bone fixation devices intraoperatively for less common types of bone fractures, and generally to provide recourse in cases in which conventional bone plates are unavailable.

SUMMARY

According to an embodiment of the present invention, a kit for the construction of a bone plate assembly for fixation of a fractured bone is provided. The kit includes a plurality of plate members, a connecting member for retaining the plurality of plate members in a desired configuration, and a plurality of locking members for securing the plate members to the connecting member.

According to one aspect of the kit, the plurality of plate members include at least two plate members.

According to another aspect of the kit, the locking members are bone screws. Each plate member includes at least one opening for retaining one of the bone screws such that the bone screws may securely attach the bone plate assembly to the fractured bone.

According to another aspect of the kit, the connecting member is flexible.

According to yet another aspect of the kit, the connecting member securely retains the plurality of plate members in a first arrangement wherein each of the plurality of plate members is moveably orientable with respect to each other such that the bone plate assembly may generally conform to the surface of the fractured bone, and wherein the locking member may fixedly secure the plate members to the connecting member in a second arrangement such that the bone plate assembly is sufficiently rigid to provide fixation of the fractured bone.

According to yet another aspect of the kit, the connecting member includes a plurality of flexible members. In the first arrangement the plurality of plate members are loosely retained on the connectors such that the flexible members may move longitudinally relative to each other, and in the second arrangement plate members are clamped tightly onto the connectors such that the flexible members are not permitted to move substantially relative to each other.

According to another aspect of the kit, each of the plurality of plate members includes a groove for receiving the connecting member.

According to yet another aspect of the kit, the plate members define a bone contacting surface and the connecting member defines a longitudinal axis of the member. The plate members also define a first dimension perpendicular to the bone contact surface and the longitudinal axis, and a second dimension parallel to the bone contact surface and the normal to the longitudinal axis, the first dimension is greater that the second dimension.

According to another aspect of the kit, the first dimension is at least twice as large as the second dimension.

According to yet another aspect of the kit, the connecting member includes a first portion, a second portion spaced from the first portion and a retainer to retain the first portion and the second portion in a spaced apart relationship.

According to another aspect of the kit, a first of the plurality of plate members defines a surface thereof, a second of the plurality of plate members defines a surface for contact with the surface of the first plate member, and the surface of the first plate member and the surface of the second plate member provide planar contact with each other.

According to yet another aspect of the kit, the plurality of plate members include a first plate member having a first shape and a second plate member having a second shape, the second shape is different than the first shape.

According to yet another aspect of the kit, the plurality of plate members include a first plate member and a second plate member, the first plate member defines a first bone contacting surface and the second plate member defines a second bone contacting surface. The first bone contacting surface and the second bone contacting surface lie in different planes.

According to another aspect of the kit, the kit further includes a second connecting member for securing the plurality of plate members to each other. The second connecting member is spaced from the first mentioned connecting member.

According to yet another aspect of the kit, the kit further includes a tray for containing the plurality of plate members, the locking members and the connecting member prior to use.

According to another aspect of the kit, the plurality of plate members include a first plate member and a second plate member, positionable adjacent the first plate member. The first plate member and the second plate member define a longitudinal axis of the plate members. The plurality of plate members also include a third plate member adjacent the first plate member and extending from the first plate member in a direction skewed with respect to the longitudinal axis of the first plate member and the second plate member.

According to yet another aspect of the kit, the kit further includes a fourth plate member adjacent the first plate member and extending from the first plate member in a direction skewed with respect to the longitudinal axis of the first plate member and the second plate member.

According to another embodiment of the present invention, a kit for use in trauma surgery for cooperation with a bone is provided. The kit includes a first plate member having a first shape and a second plate member having a second shape. The kit also includes a connecting member for securing the plurality of plate members to each other. The second shape is different than the first shape.

According to an aspect of the kit, the first plate member defines a first bone contacting surface and the second plate member defines a second bone contacting surface. The first bone contacting surface and the second bone contacting surface lie in different planes.

According to yet another aspect of the kit, the connecting member may be fixedly secured to the plurality of plate members in a first arrangement wherein each of the plurality of plate members is moveably orientable with respect to each other and in a second arrangement in which each of the plurality of plate members is rigidly secured to each other.

According to yet another embodiment of the present invention, a method of stabilizing a damaged bone is provided. The method includes the steps of providing a kit of including a tray for storing a plurality of plate members and at least one connection, at least two of the plate members having different shapes and selecting at least one plate member from the plurality of plate members and at least one connection member from the plurality of connection members. The method also includes the steps of assembling the selected at lease one plate member to the selected one connection member, placing the assembled plate and connection member against the damaged bone, and locking the plate to the connection member.

According to another embodiment of the present invention, a kit for the construction of a bone plate assembly for fixation of a fractured bone is provided. The kit includes a plurality of plate members and a flexible track for retaining the plurality of plate members in a desired configuration. The kit also includes a plurality of locking members for securing the plate members to the connecting member.

According to an aspect of the kit, the track includes a flexible retainer containing a grouping of a plurality of flexible members. The track has at least one free end.

According to another aspect of the kit, the flexible members are formed from a malleable material, such that a surgeon may shape the track into an implant configuration to conform to the fractured bone surface. Each of the plurality of plate members may be assembled to the flexible track while the flexible track is in the implant configuration.

The technical advantages of the present invention include the ability to easily shape plates without bending tools to match contours of broad bone surfaces such as on the pelvis, thereby improving fixation and reducing surgical procedure time The technical advantages of the present invention further include potential reduction of bone plate manufacturing costs and required inventory The technical advantages of the present invention further include the ability to create a wide variety of custom plates intraoperatively for less common fractures or for when conventional bone plates are not available.

The technical advantages of the present invention further include a reduction in the need to use multiple bone plates for certain types of comminuted fractures.

Other technical advantages of the present invention will be readily apparent to one skilled in the art from the following figures, descriptions and claims.

BRIEF DESCRIPTION OF THE DRAWINGS

For a more complete understanding of the present invention and the advantages thereof, reference is now made to the following description taken in connection with the accompanying drawings, in which:

FIG. 14 is a an isometric view of the bone plate assembly of FIG. 1 assembled with several plate members and shown with several bone screws inserted into the plate members;

FIG. 14A is a cross sectional view of a poly-axial bone screw that may be used with the bone plate assembly of FIG. 1;

FIG. 24 is an top view of another plate member for use with the bone plate assembly of FIG. for use on large bone surfaces;

FIG. 24A is a plan view of a connector for use with the bone plate assembly of FIG. 20.

Corresponding reference characters indicate corresponding parts throughout the several views. Like reference characters tend to indicate like parts throughout the several views.

DETAILED DESCRIPTION OF THE PREFERRED EMBODIMENTS

Embodiments of the present invention and the advantages thereof are best understood by referring to the following descriptions and drawings, wherein like numerals are used for like and corresponding parts of the drawings.

Figure 1:
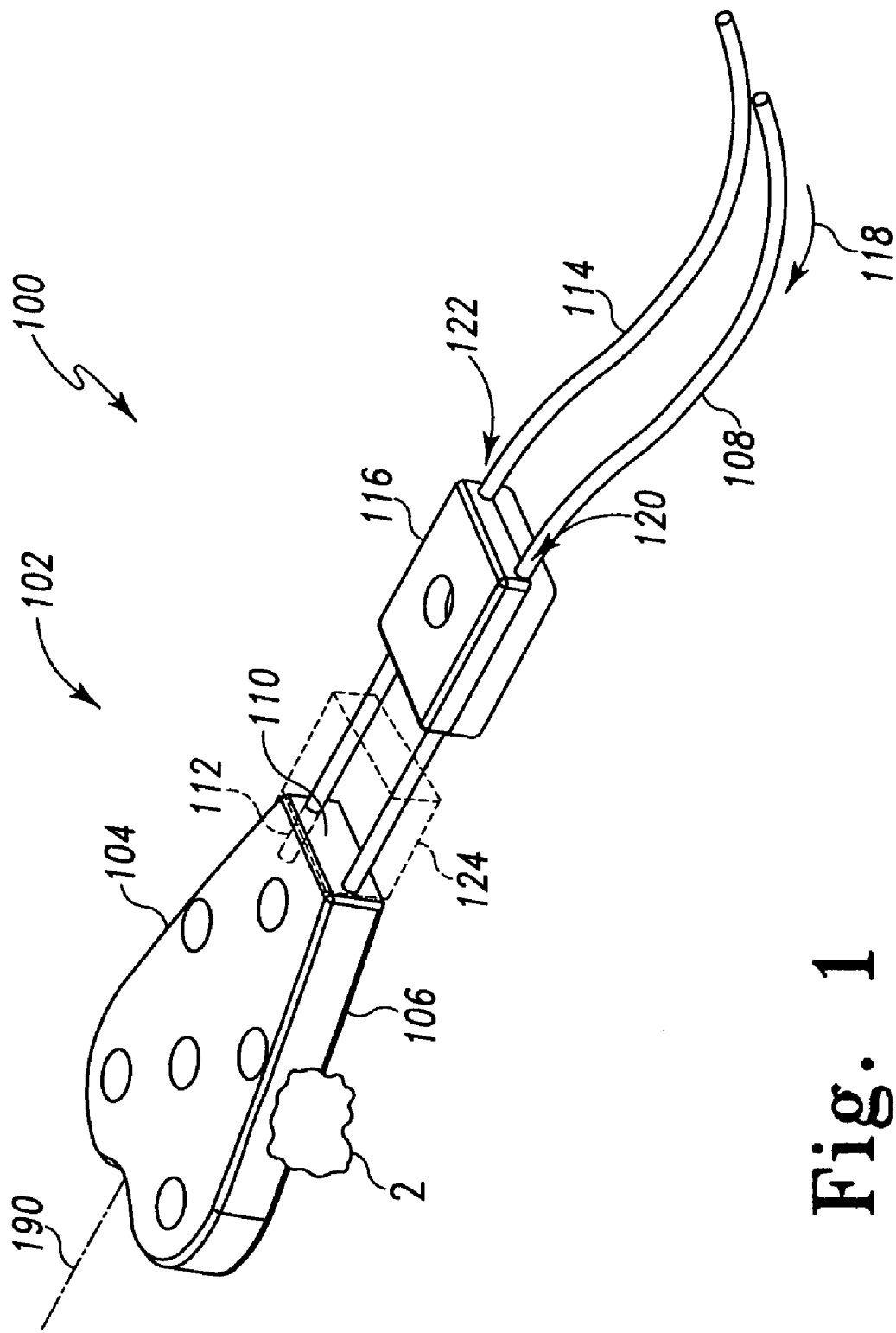
FIG. 1 is an isometric view of a portion of a bone plate assembly for repairing bone fractures including a first plate member to which a pair of spaced apart connectors are secured, a second plate member fitted to the connectors and a bone screw.

Referring now to FIG. 1 a bone plate assembly 100 according to the present invention is shown. The bone plate assembly 100 is utilized in trauma surgery for cooperation with a bone. For example, the bone plate assembly 100 may be utilized to form bone plate assembly 102.

As shown in FIG. 1, the bone plate assembly 100 includes a first plate member 104. The first plate member 104 may have been a suitable shape and may as shown in FIG. 1, have a shape suitable for contact with a condylar portion of a bone 2. For example, the first plate member 104 may have a generally truncated triangular shape such that the contact surface 106 of the plate member 104 may conform to a condylar portion of a bone.

The bone plate assembly 100 may further include a connecting member 108 for securing the plate members to each other. For example, as shown in FIG. 1, a first connecting member 108 may extend from end 110 of the first plate member 104. The first connecting member 108 may be secured to the first plate member 104 in any suitable fashion. For example, the first connecting member 108 may be interferencely fitted into opening 112 formed in first plate member 104. Alternatively, the first connecting member 108 may be welded or threadably attached to the first plate member 104.

Plate member, for example the first plate member 104 may be made of any suitable durable material. For example, the first plate member 104 may be made of a durable plastic, a composite material or a metal. The material of which the first plate member 104 is made is preferably compatible with the human anatomy and if made of a metal, the material may be, for example made of a stainless steel alloy, a titanium alloy, or a cobalt chromium alloy.

For simplicity and as shown in FIG. 1, the bone contacting surface 101 may be a planar surface. To better conform to bone, the bone contact surface 106 may be arcuate and may be generally concave to mate with a generally convex periphery of, for example, a long bone.

The first connecting member 108 may include, for example, a plurality of flexible elements that are formed, for example, from a biocompatible material such as 316L stainless steel, titanium, titanium alloy or any one of numerous polymers known in the art. The material of the flexible element may be malleable or spring-like. The flexible elements may be held together in a grouping such that the flexible elements may slide longitudinally relative to each other unless clamped tightly together by second plate member 116, whereby the clamped portion of connector 108 becomes relatively stiff. As described in the referenced patent application, the flexible elements may be clamped together to exhibit a beam stiffness that withstands a predetermined threshold force, thereby forming a suitably rigid construct for fixation of a fractured bone.

While the present invention may be practiced with a solitary connecting member 108, as shown in FIG. 1, the bone plate assembly 100 may further include the second connecting member 114. The second connecting member 114 is secured to first plate member 104. The second connecting member 114 may be made of a similar material and may be of a similar size to that of the first connecting member. The second connecting member 114 may be connected to end 110 of the first member 104 by, for example, a connection 112 in the form of an interference fit, a threaded connection or by a weldment.

As shown in FIG. 1, the bone plate assembly 100 further includes a second plate member 116. The second plate member 116 may be made of any suitable durable material and may for example be made of a metal. If made of a metal, the second plate member 116 may be made of, for example, cobalt chromium alloy steel, a stainless steel alloy or titanium alloy steel.

The first connecting member 108 and the second connecting member 114 may be, as shown in FIG. 1, formed from a flexible material. By making the first connecting member 108 and the second member 114 from a flexible material, the connecting members 108 and 114 may be positioned along the contour of the bone for which the bone plate assembly 100 is to be used. If the first connecting member 108 and second connecting member 114 are formed from a malleable material, they may be shaped like a template to generally match the contour of the bone surface. If the connecting members 108 and 114 are formed from a spring-like material, bone plate assembly 100 may tend to lift away from the bone surface until all the bone screws are inserted and tightened.

It should be appreciated that the connecting members 108 and 114 may include any of a possible number of arrangements of flexible elements. For example, the connecting members may be in the form of a circular bundle arrangement and a vertical stack arrangement. The flexible connecting members 108 and 114 may be provided with a length to build a plate assembly that is more than sufficient for the majority of surgical trauma needs. While the bone plate assembly 100 may include merely the connecting members 108 and 114, the first plate member 104 and the second plate member 116, it should be appreciated that additional plate members may be assembled onto the connecting members 108 and 116 to provide a bone plate assembly 102 of any of numerous lengths and configurations.

The second plate member 114 may be assembled onto the first connecting members 108 and the second connecting members 114 by advancing the second plate member in the direction of arrow 118. For example, the first connecting member 108 may be slidably fitted through first channel 120 formed in the second plate member while similarly, the second connecting member 114 may be slidably fitted through second channel 122 formed in the second plate member 116. The second plate member 116 is advanced in the direction of arrow 118 until the second plate member 116 is advanced to second position or assembled position 124 shown in phantom with the second plate member 116 in position against end 110 of the first plate member 104.

Referring now to FIGS. 2 through 6, the second plate member 116 is shown in greater detail. The second plate member 116 is configured to permit the second plate member 116 to slidably move along the first connecting member 108 and the second connecting member 114. It should be appreciated that the second plate member 116 may have a construction that is typical for all plate members that are to be fitted onto the first connecting member 108 and the second connecting member 114 of the bone plate assembly 102 of FIG. 1.

Figure 2:
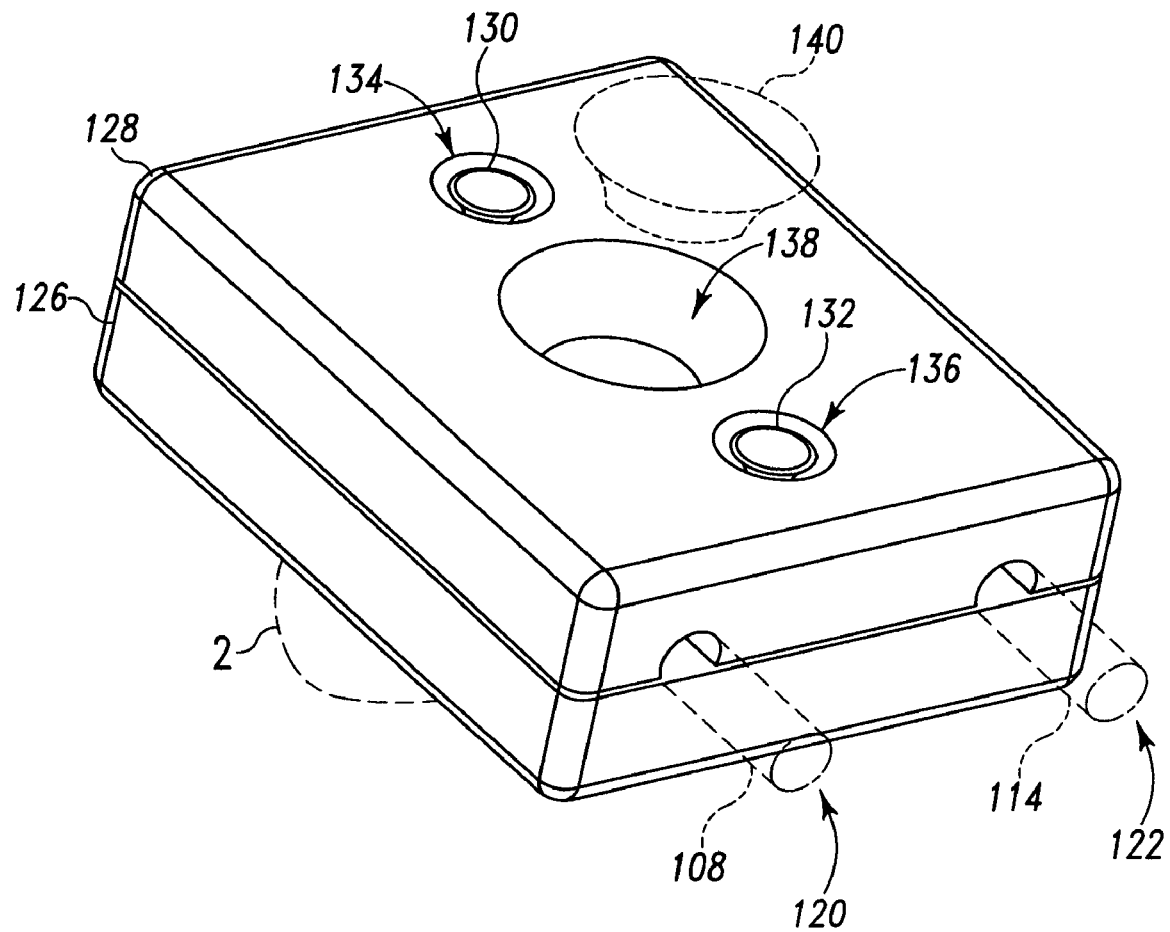
FIG. 2 is a an isometric view of the second plate member of FIG. 1 showing rivets for securing the two portions of the second plate member together.

Referring now to FIG. 2 the second bone plate 116 includes the first channel 120 and the second channel 122 to permit the sliding movement of the connecting of the second plate member 116 along the connecting members 120 and 122

The second plate member 116 as shown in FIGS. 2 through 6 is adapted to have two configurations. In a first configuration the plate member 116 may slide along the connecting members. In a second configuration the plate member 116 is fixedly secured to the connecting members. To provide the two arrangements, the second plate member 116 may be constructed of two components.

For example, as shown in FIG. 2, the second plate member 116 includes a lower plate portion 126 and an upper plate portion 128. In the first configuration, the upper plate portion 128 is permitted to move slightly with respect to the lower plate portion 126 such that the connecting members 108 and 114 may slide along the channels 120 and 122. The upper plate portion 128 is secured to the lower plate portion 126 by, for example, a first plate rivet 130 and a spaced apart second plate rivet 132. The first plate rivet 130 is fitted into first rivet opening 134 while the second plate rivet 132 is fitted into second rivet opening 136. The openings 134 and 136 are formed in the lower plate portion 126 and in the upper plate portion 128 of the second plate member 116.

The second plate member 116 may include a plate fastener opening 138 for receiving bone screw 140 for securing the second plate member 116 to bone 2. The opening 138 is formed in the lower plate portion 126 and in the upper plate portion 128 of the second plate member 116. The bone screw 140 may be in the form of a cancellous screw or a cortical screw.

Figure 3:
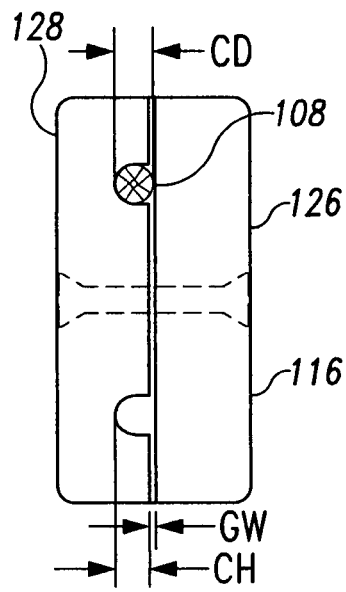
FIG. 3 is an end view of the second plate member of FIG. 2.
Figure 4:
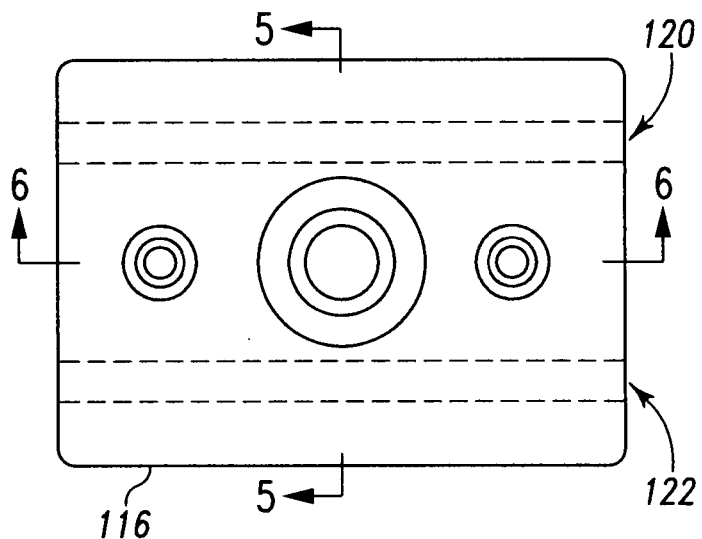
FIG. 4 is a top view of the second plate member of FIG. 2.

Referring now to FIGS. 3 through 6, second plate member 116 is shown in greater detail. Referring now to FIG. 3, the channel, for example first channel 120, defines a channel height CH. The upper plate portion 128 and the lower plate portion 126 define a space or gap having a gap width GW. The first connecting member 108 defines a connecting member diameter CD. It should be appreciated that if the connecting member diameter CD of the connecting member 108 has a dimension larger than the channel height CH when the lower plate portion 126 and the upper plate portion 128 are urged into contact in second configuration, the upper plate portion 128 and lower plate portion 126 will squeeze or hold the connecting member 108 in the channel 120.

Alternatively, when the lower plate portion 126 and the upper plate portion 128 are spaced apart, the gap width GW and the channel height CH are greater than the connecting member diameter CD of the connecting member 108. In this first configuration, the second plate member 116 is able to move in the direction 118 along the connecting members 108 and 114.

Figure 5:
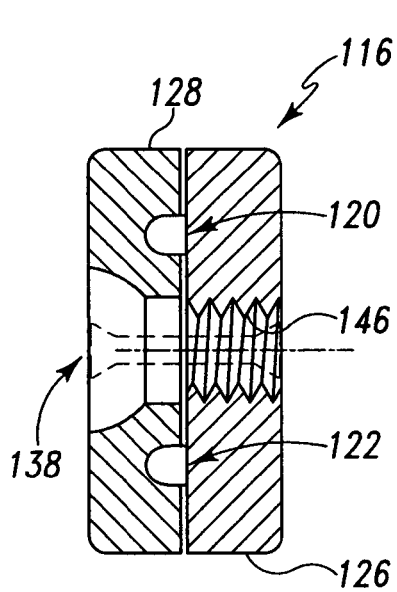
FIG. 5 is a cross sectional view of FIG. 4 along the line 5-5 in the direction of the arrows.
Figure 6:
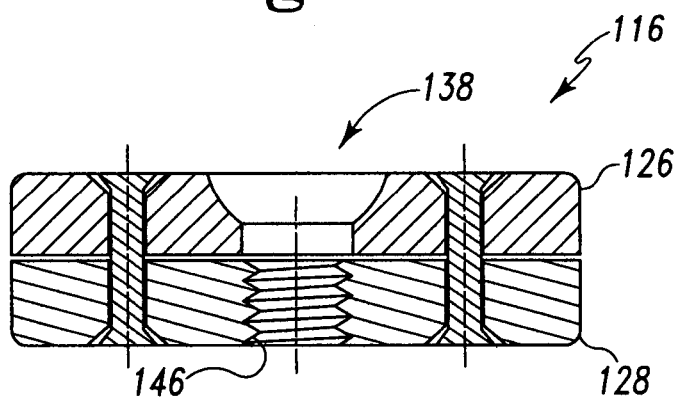
FIG. 6 is a cross sectional view of FIG. 4 along the line 6-6 in the direction of the arrows.

Referring now to FIGS. 5 and 6, the second plate member 116 includes the fastener opening 138. The fastener opening 138 cooperates with the fastener 140 to cause the upper plate portion 128 to move toward lower plate portion 126 to fixedly secure the second plate member 116 to the connecting members 108 and 114. The fastener opener 138 includes a counter bore 142 that matingly fits and holds head 144 of the bone fastener 140. The fastener opener 138 further defines internal threads 146 formed in lower plate portion 126. The internal threads 146 mate with external threads 148 formed on bone fastener 140. As the bone fastener 140 is advanced through the fastener opening 138, the external threads 148 on the bone fastener 140 cooperate with internal threads 146 on the lower plate portion 128 of the second plate member 116 to draw the upper plate portion 128 against the lower plate portion 126 to secure the second plate member 116 to the connecting members 108 and 114.

It is also possible to provide bone screw 140 with two threaded portions (not shown), wherein a first threaded portion engages the bone and a second threaded portion engages internal threads 146 of second plate member 116. With this arrangement, the type of thread of each threaded portion may be individually adapted to the desired application.

Referring now to FIGS. 7 through 13, additional plate members for use with the bone plate assembly 100 are shown. For example and referring now to FIG. 7, a third plate member 150 is shown. The third plate member 150 includes channels and a bone screw opening similar to that of the second plate member 116. The third plate member 150 includes parallel opposed first sides 152 as well as a second side set of opposed sides 154 which are not parallel with each other. By providing the third plate member 150, the bone plate assembly 102 may be configured to have a longitudinal axis that is not linear.

Figure 8:
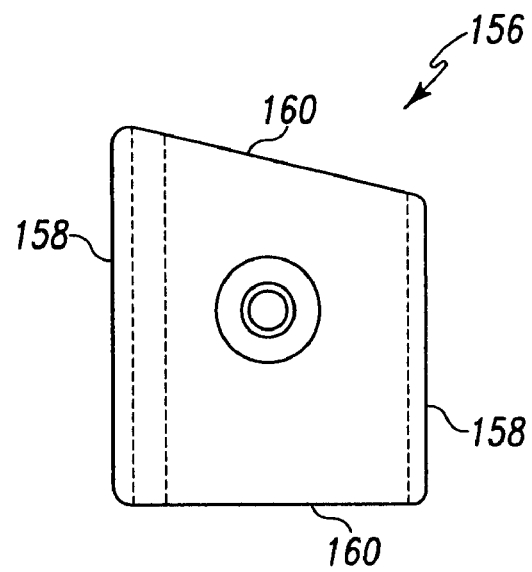
FIG. 8 is a top view of a four sided plate member with two opposed parallel sides and two opposed non parallel sides.

Referring now to FIG. 8, yet another plate member for use in bone plate assembly 102 is shown as fourth plate member 156. The fourth plate member 156 has a pair of channels and a bone screw opening similar to that of the second plate member 114 and includes a first set of parallel sides 158 as well as a third and fourth opposed set of sides 160 which are not parallel.

Figure 9:
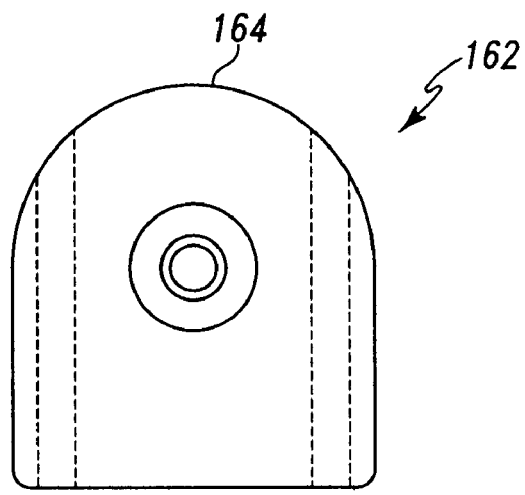
FIG. 9 is a top view of a four sided plate member with two opposed parallel sides, a third normal side and a fourth curved side.

Referring now to FIG. 9, yet another plate member is shown as fifth plate member 162. The fifth plate member 162 includes a side 164 which is curved or arcuate. The arcuate surface 164 may be utilized at the end of distal portion of the bone plate assembly 102.

Figure 10:
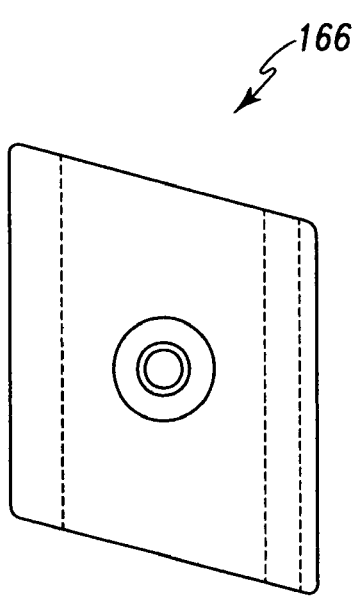
FIG. 10 is a top view of a four sided plate member with two opposed parallel sides and two opposed non parallel sides.

Referring now to FIG. 10 a plate member with yet another shape is shown as sixth plate member 166. The sixth plate member 166 has a shape generally that of a parallelogram.

Figure 11:
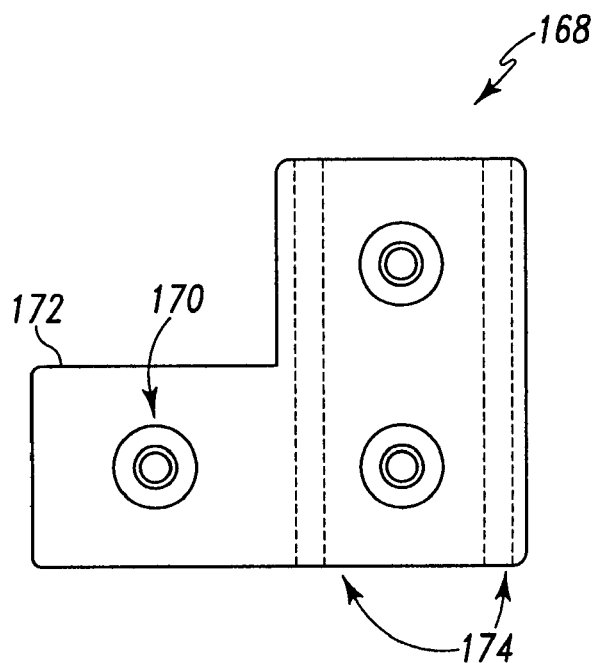
FIG. 11 is a top view of an L-shaped plate member.

Referring now to FIG. 11 yet another plate member is shown as seventh plate member 168. The seventh plate member 168 is generally L-shaped and includes an opening 170 in a bone portion 172 that extends outwardly or beyond the channels 174 of the seventh plate member 168.

Figure 12:
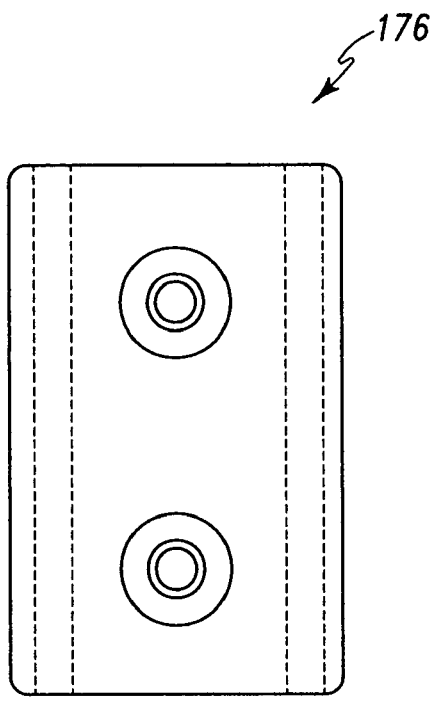
FIG. 12 is a top view of a rectangular shaped plate member.

Referring now to FIG. 12 yet another plate member is shown as eighth plate member 176. The eighth plate member 176 includes two spaced apart bone screw openings and is rectangular.

Figure 13:
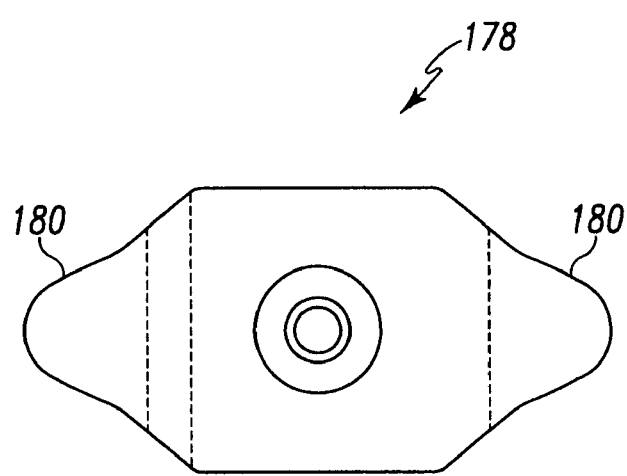
FIG. 13 is a top view of a plate member with two opposed parallel sides and two opposed arcuate sides.

Referring now to FIG. 13 yet another plate member is shown as ninth plate member 178 which includes opposed wings 180.

FIG. 14 shows the completed bone plate assembly 102, in which the second plate member 116 abuts against first plate member 104 such that a minimal length of connectors 108 and 114 are exposed, thereby maximizing the rigidity of the assembly. Another plate member, for example fourth plate member 156 of FIG. 8, is positioned tightly against second plate member 116. An additional plate member, for example another second plate member 116, is positioned against fourth plate member 156. A tenth plate member 182 having a configuration which is a mirror image of that of a fourth plate member 156 may be positioned against second plate member 116. For example third plate member 150 may be positioned against the tenth plate member 180. Finally, fifth plate member 162 having the arcuate portion 164 may be positioned against third plate member 150. The seven plate members shown in FIG. 14 are urged against each other and the excess portions 183 of the first connector 108 and second connector 114 are preferably removed by, for example, a conventional surgical wire cutting tool (not shown) such that a unitary bone plate or a rigid bone plate assembly 102 is provided.

Referring now to FIG. 14A a poly-axial screw assembly 140A is shown. The poly-axial screw assembly 140A may be used as a substitute to bone screw 140 or may be used in addition to bone screw 140. A single assembly 140A may be used or a plurality of assemblies 140A may be positioned as desired on the plate assembly 102. The assembly 140A includes a bushing 137A with a spherical periphery 138A that swivels in a spherical pocket 139A formed in plate member 104A. The bushing 137A is split and expands to lock screw 142A into any one chosen of a multitude of angles by a tapered threaded head 141A on screw 142A with engages tapered threads 143A formed in hole 145A in bushing 137A. A more thorough description of a poly-axial bushing may be found in U.S. Pat. No. 5,954,722 to Bono and in US Patent Application Publication No. 2005/0049594 to Wack et al., both hereby incorporated by reference in their entireties.

Figure 15:
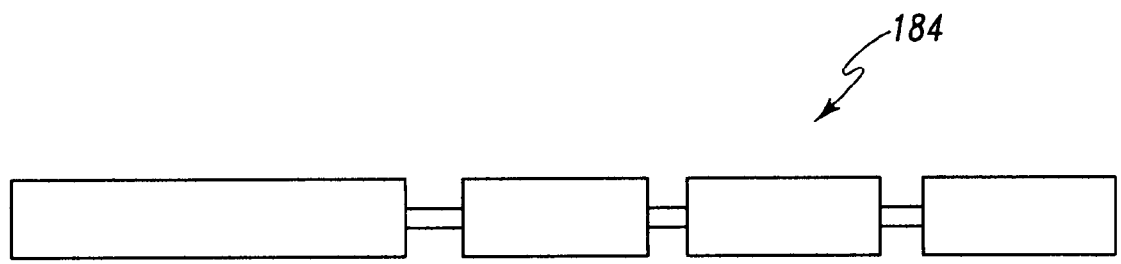
FIG. 15 is a partial top view of the bone plate assembly of FIG. 14 with the plate members in a slightly spaced apart relationship to show a flexible plate assembly.
Figure 16:
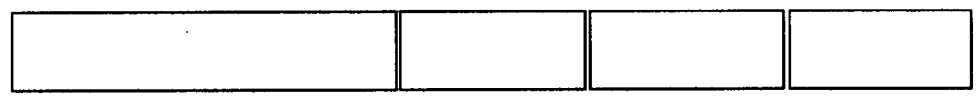
FIG. 16 is a partial top view of the plate assembly of FIG. 14 with the plate members in a touching relationship to show a rigid plate assembly.

Referring now to FIGS. 15 and 16, the bone plate assembly 102 is shown in FIG. 15 in a first configuration 184 in which adjacent bone plate members are spaced from each other in this configuration the bone plate may be conformed to the shape of the bone. The first configuration 184 may have the necessary rigidity to form a stable, fixation construct on the fractured bone, although the rigidity of bone plate assembly 102 as shown in FIG. 15 depends largely on the material and design of connectors 108 and 114. Referring now to FIG. 16 the bone plate assembly 102 is shown in a second configuration 186. In second configuration 186 adjacent plate members are positioned in abutment or close proximity to each other such that the individual bone plates together with the connection members provide for a rigid construction to support the bone.

Figure 6A:
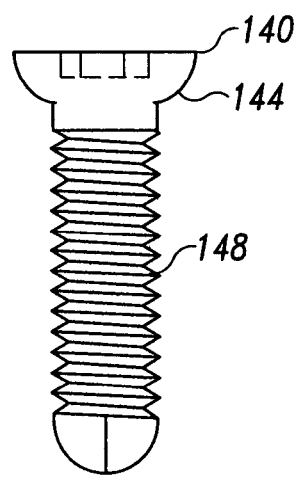
FIG. 6A is a plan view of a fastener for use with the plate member of FIG. 2.
Figure 7:
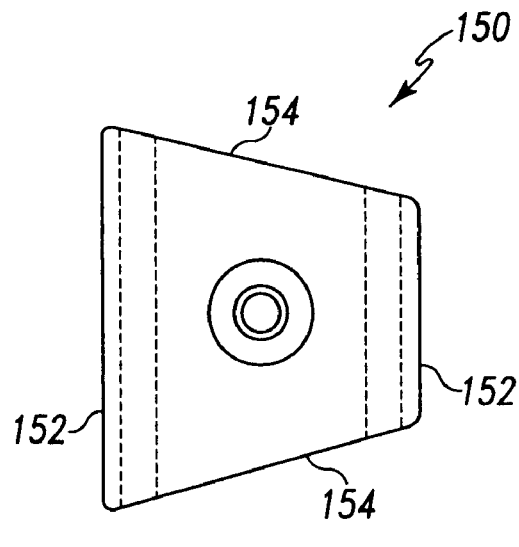
FIG. 7 is a top view of a four sided plate member with two opposed parallel sides and two opposed non parallel sides.
Figure 16A:
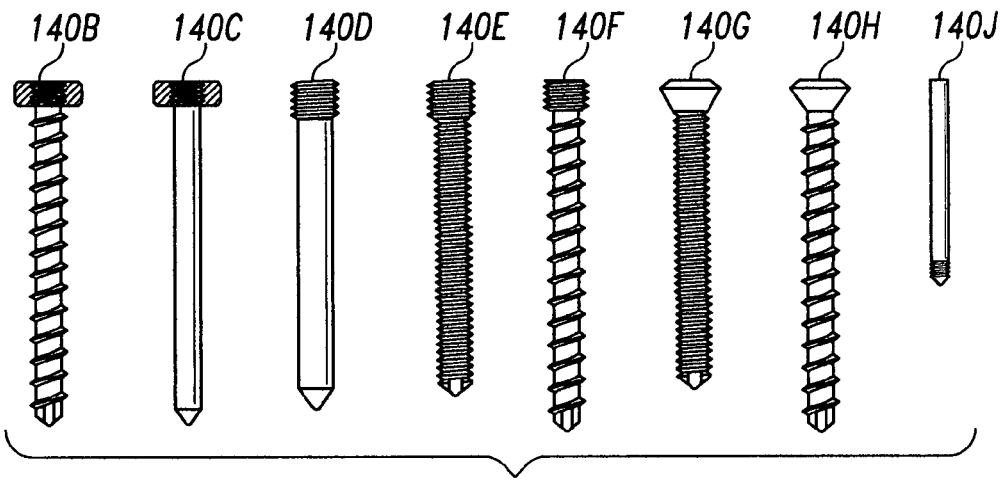
FIG. 16A is a plan view of alternate bone screws and pins that may be used with the bone plate assembly of FIG. 1.

Referring now to FIG. 16A, alternate fasteners to bone screw 140 of FIG. 6A are shown. It should be appreciated that the bone screw 140 may be substituted by poly-axial cancellous bone screw assembly 140B, by poly-axial bone pin assembly 140C, by locked bone pin 140D, by locked cortical bone screw 140E, by locked cancellous bone screw 140F, by un-locked cortical bone screw 140G, by un-locked cancellous bone screw 140H.

Continuing to refer to FIG. 16A, it should be appreciated that small holes may be placed in the bone plate 104 of FIG. 1 to receive, for example, guide pins, for example, guide pin 140J.

Figure 16B:
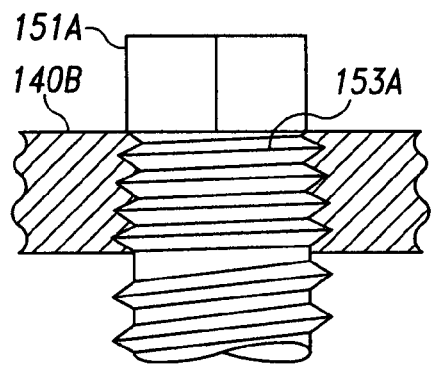
FIG. 16B is a plan view of a bushing that may be used with the bone plate assembly of FIG. 1.

Referring now to FIG. 16B, it should further be appreciated that the bone plate 104 of FIG. 1 may utilize bushing that may be placed in the opening of the plate 104 to receive drills and reamers to prepare the holes for receiving the bone screws and the bone pins. For example a bushing 151A may be threadably engaged by threads 153A to bone plate 104B to guide a drill (not shown). A more thorough description of a guide bushing may be found in US Patent Application Publication No. 2006/0149250 to Castaneda et al., hereby incorporated by reference in its entirety.

Figure 17:
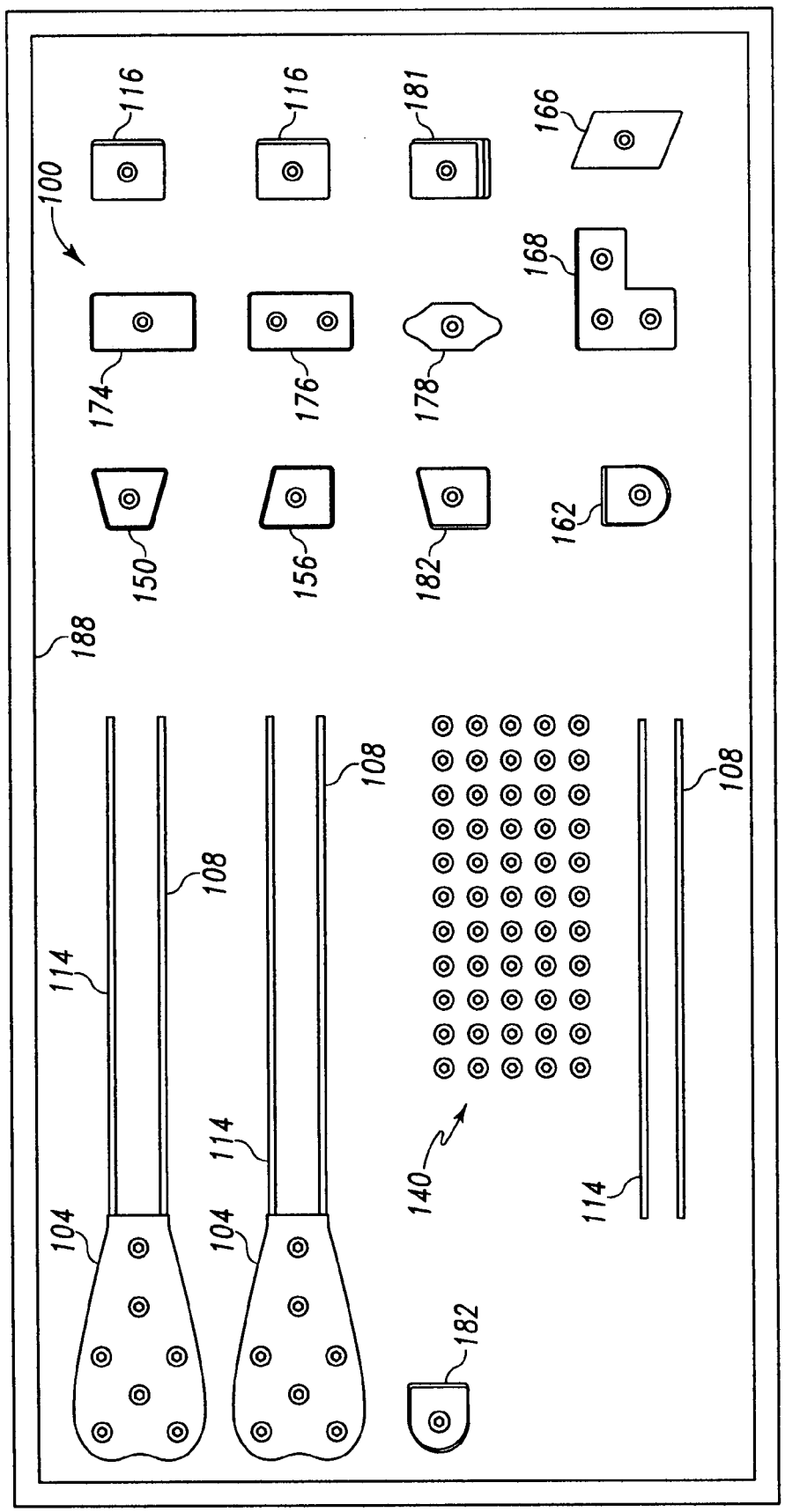
FIG. 17 is a top view of the plate kit of FIG. 1 disassembled with several plate members to form a plate kit with the kit components placed in a sterilization tray.

FIG. 17 shows a bone plate assembly kit 101 from which components may be selected for assembling the bone plate assembly 100 of FIG. 1. Kit 101 includes a tray 188 similar to those known in the art for organizing orthopaedic devices to be used in a specific surgical procedure. Tray 188 and its components may be constructed of materials that can withstand many cycles of steam autoclave sterilization.

As shown in FIG. 17, the kit 101 may include the first plate member 104. It should be appreciated that a plurality for example two first plate members 104 may be included in the kit 101. It should also be appreciated that the additional plate members, for example second plate member 116, may be included in the kit 101 and, for example, a plurality, for example, two second plate members 116 may be included in the kit 101. Similarly the kit 101 may include one or more third plate members 150, fourth plate members 156, fifth plate members 162, sixth plate members 166, seventh plate members 178, eighth plate members 176, as well as, ninth plate members 178. It should be appreciated that tenth plate member 182 may also be included in the kit, as well as additional plate members, for example plate members 179 and 181. It should be appreciated as shown in FIG. 17, that first connector member 108 and second connecting member 114 may be of sufficient length to accommodate the longest possible bone plate assembly that reasonably may be needed by the surgeon to perform trauma surgery. The kit 101 may also include bone screws 140 for use with the plate members. It should be appreciated that the bone screws 140 may all be of the type of FIG. 6A and may be of varying lengths and sizes to accommodate different bones and different portions of bone. Further it should be appreciated that the bone screws may be of other types such as those shown in FIG. 16A While the bone plate assembly 100 of FIGS. 1 to 17 is well suited for bone plates where the bone contact surface of bone 2 is generally planar, it should be appreciated that bone plates to accommodate bones that cover a plurality of planes is desired. Such bones may include the shaft and condylar portions of long bones and bones with irregular shapes, for example bones associated with the pelvis.

Figure 18:
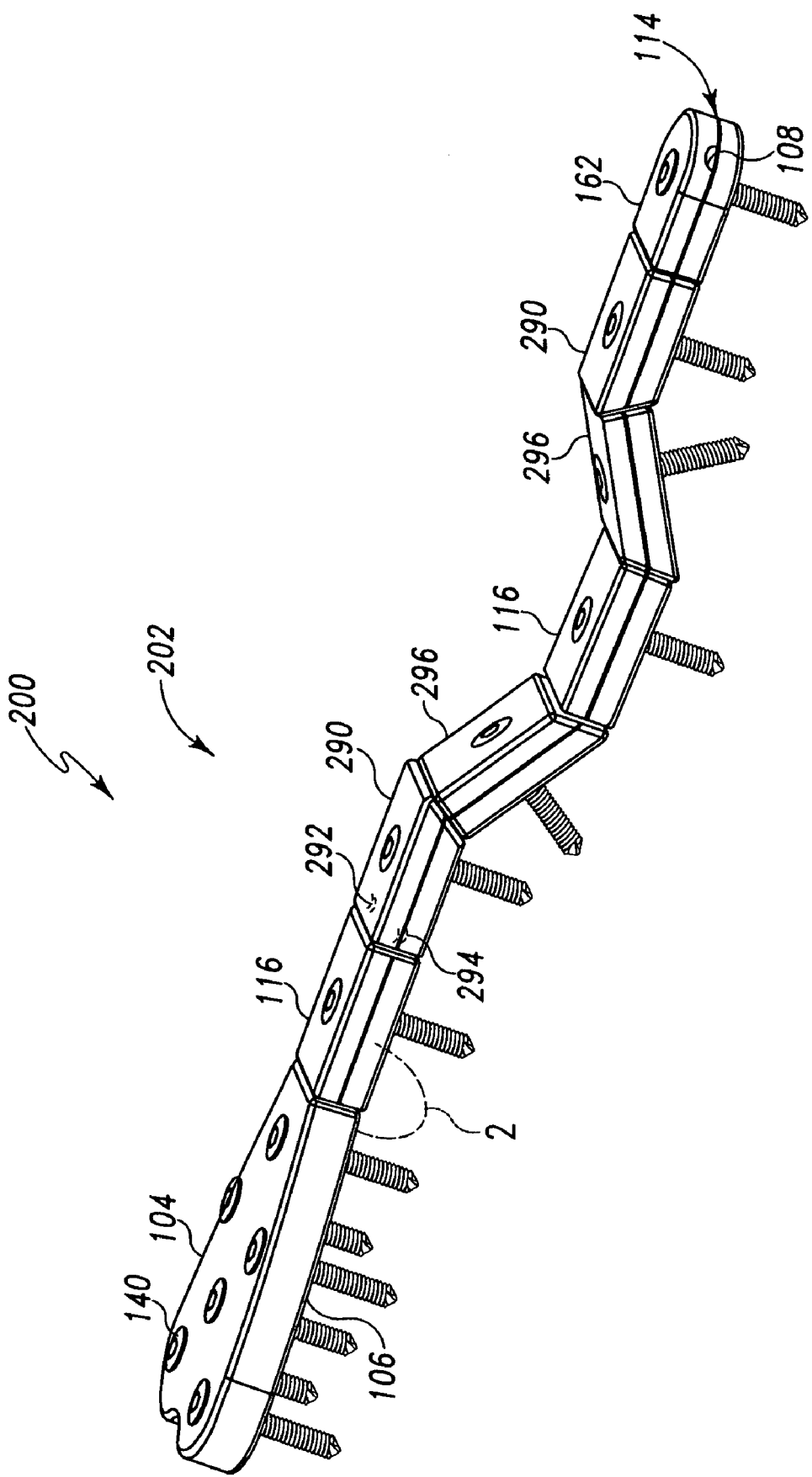
FIG. 18 is a an isometric view of a bone plate assembly according to another embodiment of the present invention including components of the kit of FIG. 1 as well as additional components for use on a non-planar bone surface.
Figure 19:
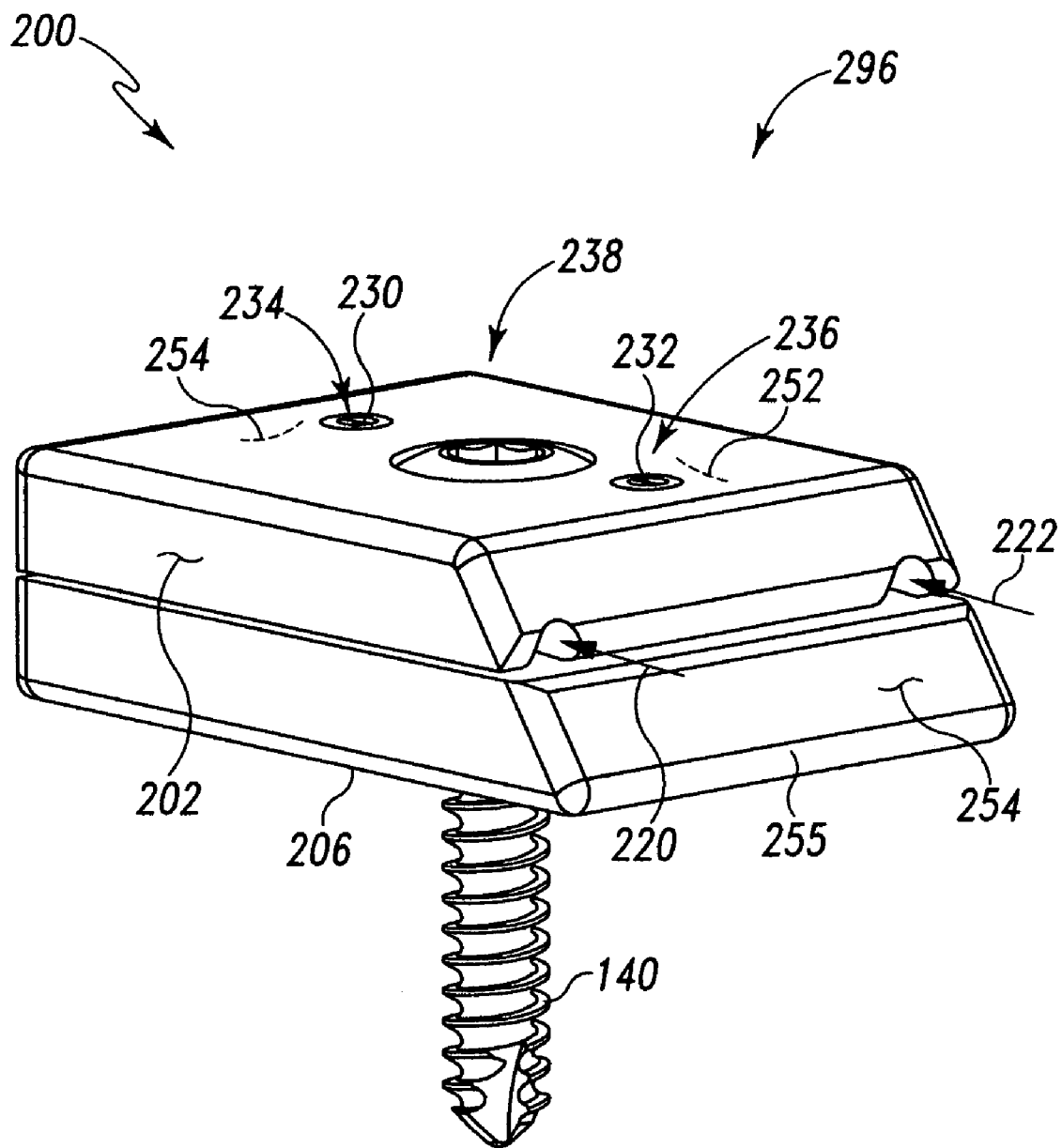
FIG. 19 is an isometric view of a plate member for use with the bone plate assembly of FIG. 18 for use on a non-planar bone surface.

For example, and is shown in FIGS. 18 and 19 yet another embodiment of the present invention is shown as bone plate assembly 200. The bone plate assembly 200 is utilized to prepare a bone plate assembly 202 which provides for bone contact surfaces on a plurality of planes.

For example, FIG. 18 shows a bone plate assembly 200 that uses components from the kit 101. For example, the bone plate assembly 200 may include first plate member 104 from the kit 101. The first plate member 104 includes the first connecting member 108 as well as the spaced apart second connecting member 114. Additional bone plate members may be assembled in sequence onto the connecting members 108 and 114 by feeding the connecting members 108 and 114 through the channels formed in the plate members. If connecting members 108 and 114 are formed from a malleable material, they may pressed against the bone surface and hand-shaped to match the contours of the bone surface, then removed from the bone surface so that the plate members may easily be slid onto them in the proper sequence. The loose assembly may then be positioned on the bone surface and attached to the bone with the bone screws. As each bone screw is tightened, the respective plate member clamps tightly onto the connectors to stiffen that portion of the bone plate assembly.

As shown in FIG. 18, the second bone plate 116 may be positioned adjacent first plate member 104. Similarly as to the plate 102 of the kit 101 of FIGS. 1 through 17, the bone plate assembly 200 of FIGS. 18 and 19 is utilized by positioning the first connecting member 108 and the second connecting member 114 along the bone 2. The malleable connecting members 108 and 114 are positioned adjacent to bone such that when the plate member 114 is assembled onto the connecting members 108 and 114, the plate member closely conforms to the bone.

The bone plate assembly 200 as shown in FIG. 18 further includes a first non-planar plate member 290 which includes first and second parallel faces 292 as well as non-parallel faces 294. The first non-planar plate member 290 is positioned against second plate member 116. A second non-planar plate member 296 is positioned adjacent the first non-planer plate member 290. An additional second plate member 116 is positioned adjacent the second non-planar plate member 296. An additional second non-planar plate member 296 is positioned adjacent the second place member 116. Similarly a second first non-linear plate member 290 is positioned adjacent the second non-planar plate member 296. A fifth planer member 162 is positioned adjacent the first non-planar plate member 292 for the plate assembly 202 of FIG. 18.

After the fifth plate member 162 is positioned adjacent the first non-planar plate member 290, the additional portions 183 of the first connecting member 108 and the second connecting member 114 are removed by for example a surgical wire cutting tool which trims off the excess of the flexible member that extends beyond the plate member 162.

Referring now to FIG. 19 the second non-planar locking plate member 296 is shown in greater detail. The plate member 296 includes a bone fastener opening 238 for receiving for example bone fastener 140. The plate member 296 further includes first rivet opening 234 that receives first rivet 230, as well as second rivet opening 236 that receives second rivet 232. The plate member 296 further includes first channel 220, as well as spaced apart second channel 222. The plate member 296 further includes first and second parallel sides 252, as well as non-parallel sides 254. The non-parallel sides 254 include a side 255 which is not perpendicular with bone contact surface 206 of the plate member 296.

While the plate assembly 202 of the bone plate assembly 200 of FIGS. 18 and 19 and the bone plate assembly 100 of FIGS. 1 through 17 may be suitable for many bone fractures, for those situations in which the area in both the X direction and Y direction for the fracture is large a bone plate may be necessary with greater width and yet, considerable length. Such a situation may occur in a fracture of the pelvis.

Referring now to FIGS. 20 through 25, another embodiment of the present invention is shown as a bone plate assembly 300, which may provide three-dimensional fixation of a fracture on a broad, contoured surface of a bone such as the ilium.

Figure 20:
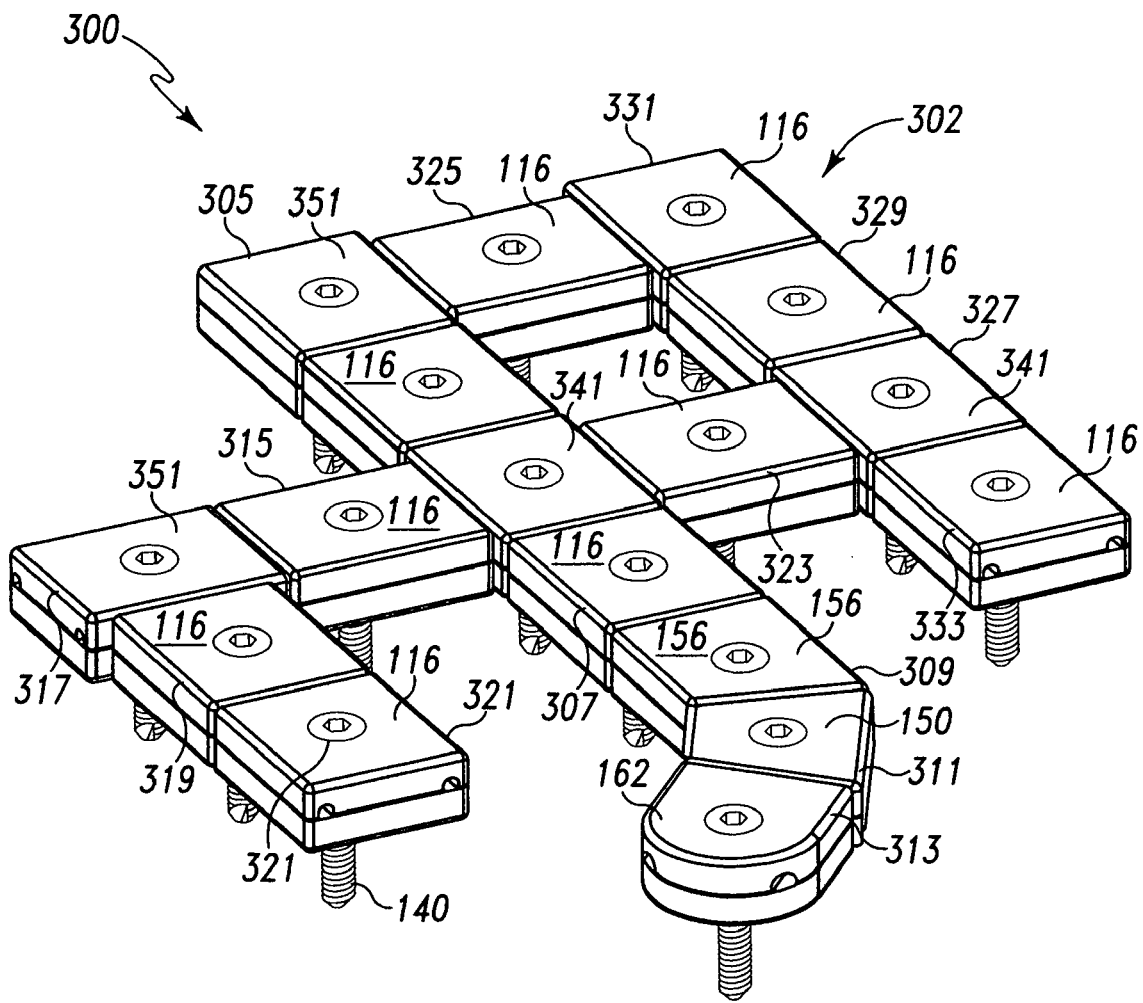
FIG. 20 is a an isometric view of a bone plate assembly according to another embodiment of the present invention including components of the kit of FIG. 17 as well as additional components for use on large bone surfaces.

For example, and as shown in FIG. 20, the bone plate assembly 300 may include a first bone plate 301 a second bone plate 303, and a third bone plate 305 connected to the second bone plate 303. The kit also includes a fourth bone plate 307 connected to the first bone plate 301, a fifth bone plate 309 connected to the fourth bone plate 307, a sixth bone plate 311 connected to the fifth bone plate 309, and a seventh bone plate 313 connected to the sixth bone plate 311.

The bone plate assembly 300 may further include an eighth bone plate 315 connected to the first bone plate 301, a ninth bone plate 317 connected to the eighth bone plate 315, a tenth bone plate 319 connected to the ninth bone plate 317 and an eleventh bone plate 321 connected to the tenth bone plate 319. The bone plate assembly 300 may further include a twelfth bone plate 323 connected to the first bone plate 301 and a thirteenth bone plate 325 connected to the third bone plate 305. The bone plate assembly 300 may further include a fourteenth bone plate 327 connected to the twelfth bone plate 323, a fifteenth bone plate 329 connected to the fourteenth bone plate 327 and a sixteenth bone plate 331 connected both to the thirteenth bone plate 325 and the fifteenth bone plate 329. The bone plate assembly 300 may further include a seventeenth bone plate 333 connected to the fourteenth bone plate 327. While the bone plate assembly 300 may be made, as shown in FIG. 20, of planar plate members, it should be appreciated that non-planar members, such as the plate member 296 of FIG. 19, may be used with the bone plate assembly 300.

Figure 21:
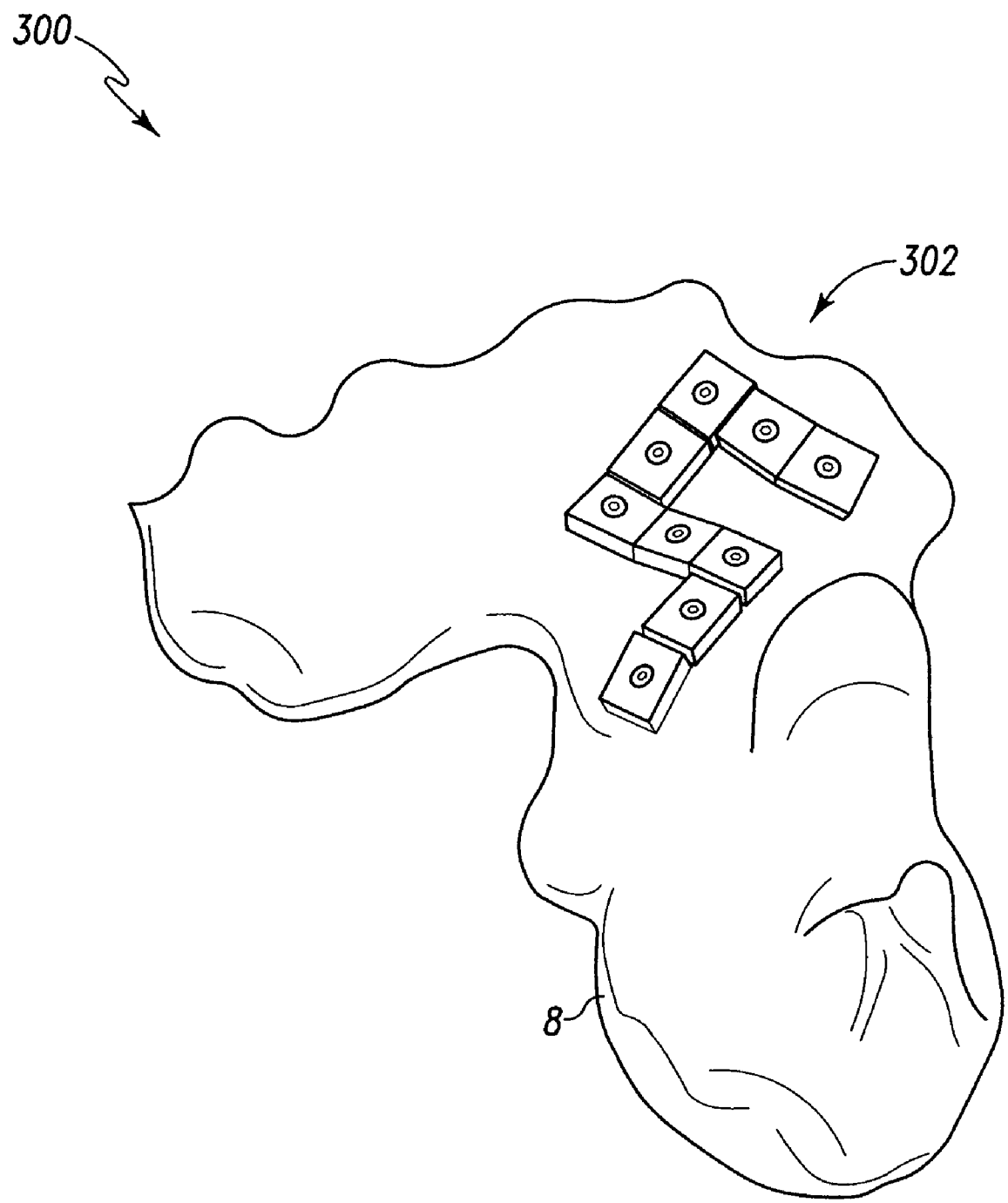
FIG. 21 is a an isometric view of the bone plate assembly of FIG. 20 attached to the surface of the ilium for repair of an acetabular fracture.

Referring now to FIG. 21, the plate assembly 302 is shown attached to an ilium 8 of a patient. It should be seen that the plate assembly 302 may follow a plurality of planes to conform to the contour of the ilium 8 or other broad bone surfaces.

The bone plate assembly 300 like the bone plate assembly 200 of FIGS. 18 and 19 and the bone plate assembly 100 of FIGS. 1-17 may include components of the bone plate assembly 200 and the bone plate assembly 100. The bone plate assembly 300 may for example include bone screws 140 as well as rectangular bone plates 116. The bone plate assembly 300 includes bone plates to provide for connection of bone plates both in a line and in a second line normal to the first line to form a grid of bone plates.

Figure 22:
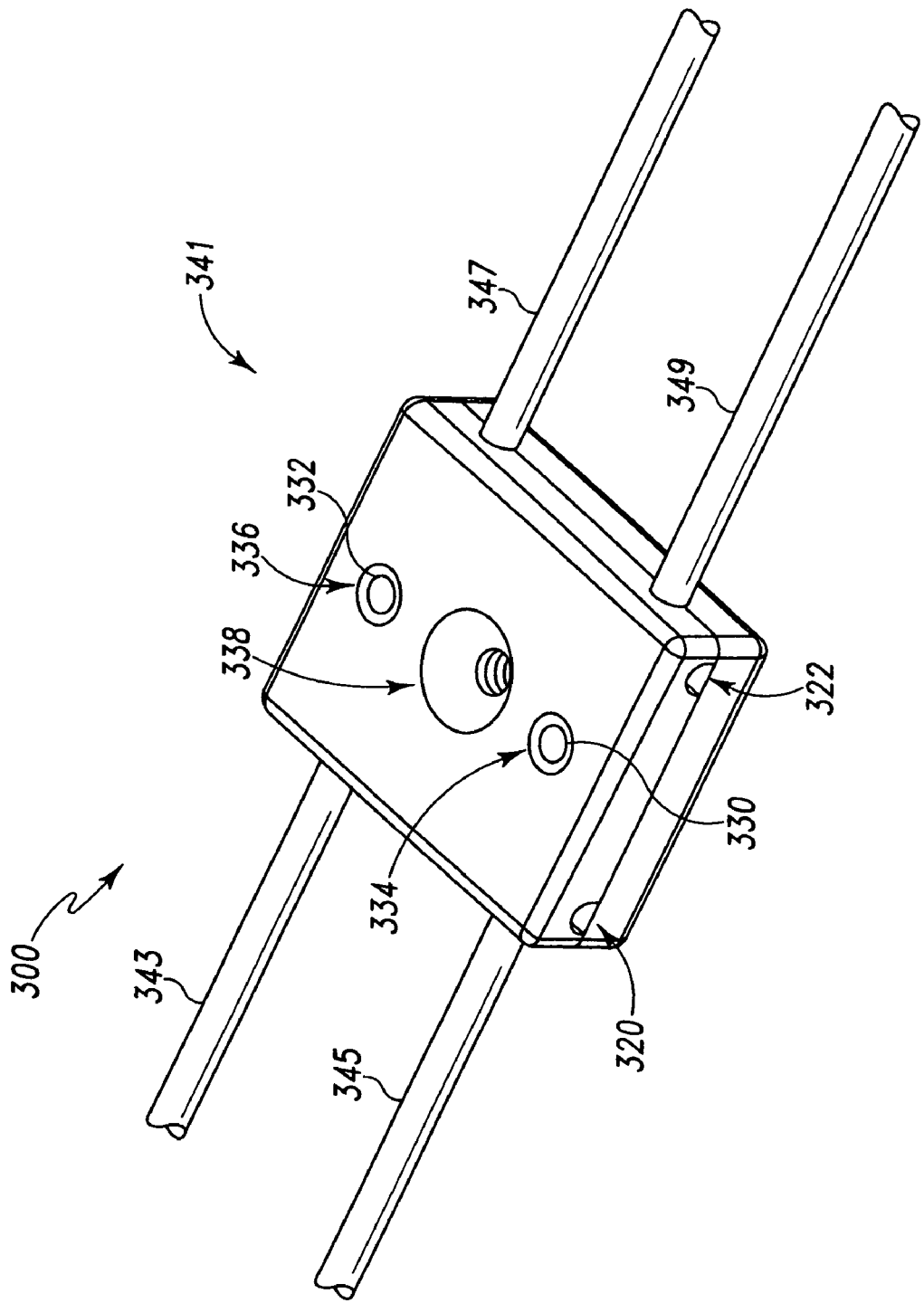
FIG. 22 is an isometric view of a plate member for use with the bone plate assembly of FIG. 20 for use on large bone surfaces.
Figure 23:
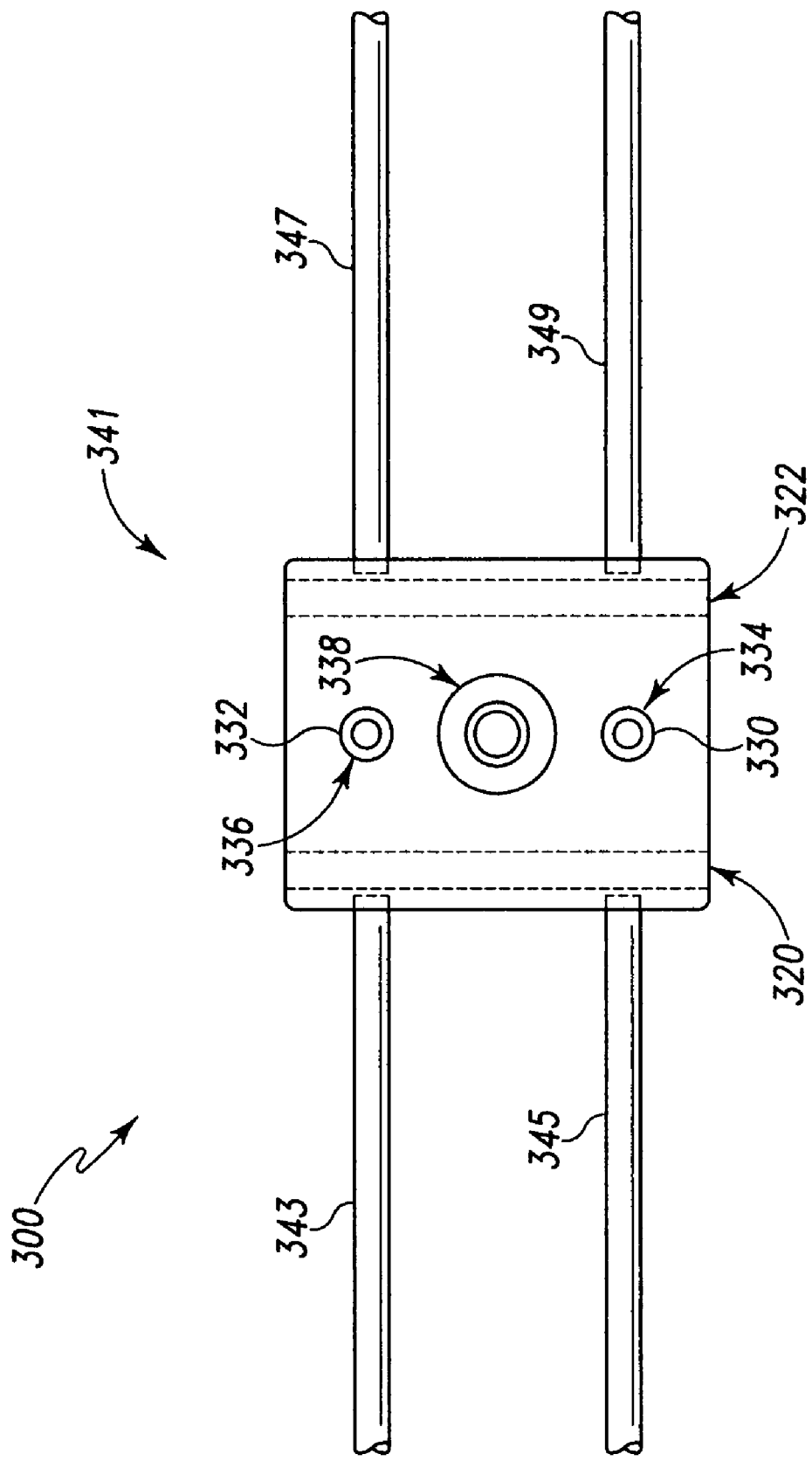
FIG. 23 is a top view of the plate member of FIG. 22.

For example and as shown in FIGS. 22 and 23, the bone plate assembly 300 may include an X type bone plate 341. The bone plate member 341, as shown in FIGS. 22 and 23 includes first channel 320, as well as spaced apart second channel 322. The plate member 341 may further include a first connector 343 which extends from plate member 341.

The plate member 341 may further include a second connector 345 spaced from and parallel to the first connector 343. The first connector 343 and second connector 345 are perpendicular to the first channel 320 and the second channel 322 to form a rectangular grid for the assembling of plate members. The plate member 341 may further include a third connector 347 extending from the plate member 341 in a direction opposed to first connector 343. Similarly the plate member 341 may further include a fourth connector 349 extending from the plate member 341 in a direction opposed to the second connector 345.

The plate member 341, similarly to the plate member 160 of FIG. 2, may include a first rivet 330 and a spaced apart second rivet 332. The first rivet 330 fits into first rivet opening 334 while the second rivet 332 fits into second rivet opening 336. The plate number 342 further includes a fastener opening 338 for use with plate fastener 140.

Referring now to FIG. 24 yet another plate member for use with the bone plate assembly 300 is shown as T shaped plate member 351. The T shaped plate member 351 includes a first channel 353 and a spaced apart second channel 355. The plate member 351 further includes a first connector 357 positioned perpendicular to first channel 353 and a second connector 359 extending from the plate member 351 in a direction parallel to first connector 357. The T shaped plate member 351 further includes a bone fastener opening 361 for receiving the bone screw 140.

Referring now to FIG. 24A the bone plate assembly 300 may further include solitary connectors 363 for use with the bone plate assembly 300.

Referring again to FIG. 20, the plate assembly 302 may be assembled in various orders. For example, the third plate member 305, which may be in the form of T shaped plate member 351 as shown in FIG. 24, is utilized. The second plate member 303 which may be in the form of plate member 116 of FIG. 2 is assembled against third plate member 305 by inserting the first connector 357 and the second connector 359 of the first plate member 305 into the channels in the second plate member 303.

Next, the first plate member 301 is connected to the second plate member 303. The first plate member 301 may be in the form of an X plate member 341, as shown in FIG. 22. The first plate member 301 is assembled to the second plate member 303 by inserting the first connector 357 and the second connector 359 into the channel 320 and 322 of the X plate member 301. The fourth plate member 307, which may be in the form of 116 of FIG. 2, is assembled against first plate member 301 by positioning the first connector 357 and the second connector 359 into the channels of the fourth plate member 347.

Next, the fifth plate member 309, which may be in the form of plate member 156 of FIG. 8, is positioned in fourth plate member 307. The first connector 357 and the second connector 359 are inserted into channels formed in fifth plate member 309. Next, the sixth plate member 311 is secured against fifth plate member 309. The sixth plate member 311 may be in the form of plate member 150 of FIG. 7. The sixth plate member 311 is secured to the fifth plate member 309 by positioning the first connector 357 and the second connector 359 into the channels formed in the sixth bone plate 311.

Next the seventh bone plate 313, which may be in the form of bone plate 162 of FIG. 9, is secured against sixth bone plate 311 by inserting the first connector 357 and the second connector 359 into channels formed in the seventh bone plate 313. Next, the eighth bone plate 315 is secured to the first bone plate 301. The eighth bone plate 315 may be in the form of bone plate 116 of FIG. 2. The bone plate 315 is secured to the first bone plate 311 by inserting the first connector 343 and the second connector 345 into channels formed in the bone plate 315.

Next the ninth bone plate 317 is secured to the eighth bone plate 315. The ninth bone plate 317 may be in the form of T plate member 351 as shown in FIG. 24. The ninth bone plate 317 is secured to the eighth bone plate 315 by inserting the first connector 343 and the second connector 345 into the channels formed in the bone plate 300 ninth bone plate 317. Next the tenth bone plate 319 is secured to the ninth bone plate 317. The tenth bone plate 319 may be in the form of bone plate 316 of FIG. 2. The tenth bone plate 319 is secured to the ninth bone plate 317 by inserting the first connector 357 and the second connector 359 into the channels formed in the tenth bone plate 319. Next, the 11th bone plate 321 which may be in the form of plate 116 of FIG. 2 is secured to the tenth bone plate 319 by inserting the first connector 357 and the second connector 369 into cavities into channels formed in 11th bone plate 321.

Next the twelfth bone plate is secured to the first bone plate 301. The twelfth bone plate 323 may be in the form of bone plate 116 of FIG. 2. The twelfth bone plate 323 is secured to the first bone plate 311 by inserting the third connector 347 and the fourth connector 349 into channels formed in the twelfth bone plate 323. Next, the fourteenth bone plate is connected to the fifteenth bone plate. The fourteenth bone plate 327 may be in the form of a T shaped bone plate 351 see FIG. 24. The fifteenth bone plate 329 may be in the form of bone plate 116 of FIG. 2. The fifteenth bone plate 329 is secured to the fourteenth bone plate 327 by inserting the first connector 343 and the second connector 345 into channels formed in fifteenth bone plate 329. The sixteenth bone plate 331 may then be secured to the fifteenth bone plate 329.

The sixteenth bone plate 331 may be in the form of a T shaped plate member 351 as shown in FIG. 24. The sixteenth bone plate 331 is connected to the fifteenth bone plate 329 by inserting first connector 343 and second connector 345 into channels formed in the sixteenth bone plate 331. Next, the seventeenth bone plate 333 is connected to the fourteenth bone plate 327. The seventeenth bone plate 333 may be in the form of bone plate 116 as shown in FIG. 2. The seventeenth bone plate 333 is connected to the fourteenth bone plate 327 by inserting third connector 347 and fourth connector 349 into channels formed in seventeenth bone plate 333.

The thirteenth bone plate is next connected to the sixteenth bone plate 331. The thirteenth bone plate 325 may be in the form of bone plate 116 of FIG. 2. The thirteenth bone plate 325 is secured to the sixteenth bone plate 116 by inserting fifth first connector 357 and second connector 359 into channels formed in thirteenth bone plate 325. Next, the assembly of the 13$^{th}$, 14$^{th}$, 15$^{th}$, 16$^{th}$, and 17$^{th}$ bone plates is inserted into the assembly of the remaining bone plates by inserting the first connector 357 and the second connector 359 into channels formed in third bone plate member 305 and inserting connectors 347 and 349 into channels formed in fourteenth bone plate 327.

Figure 25:
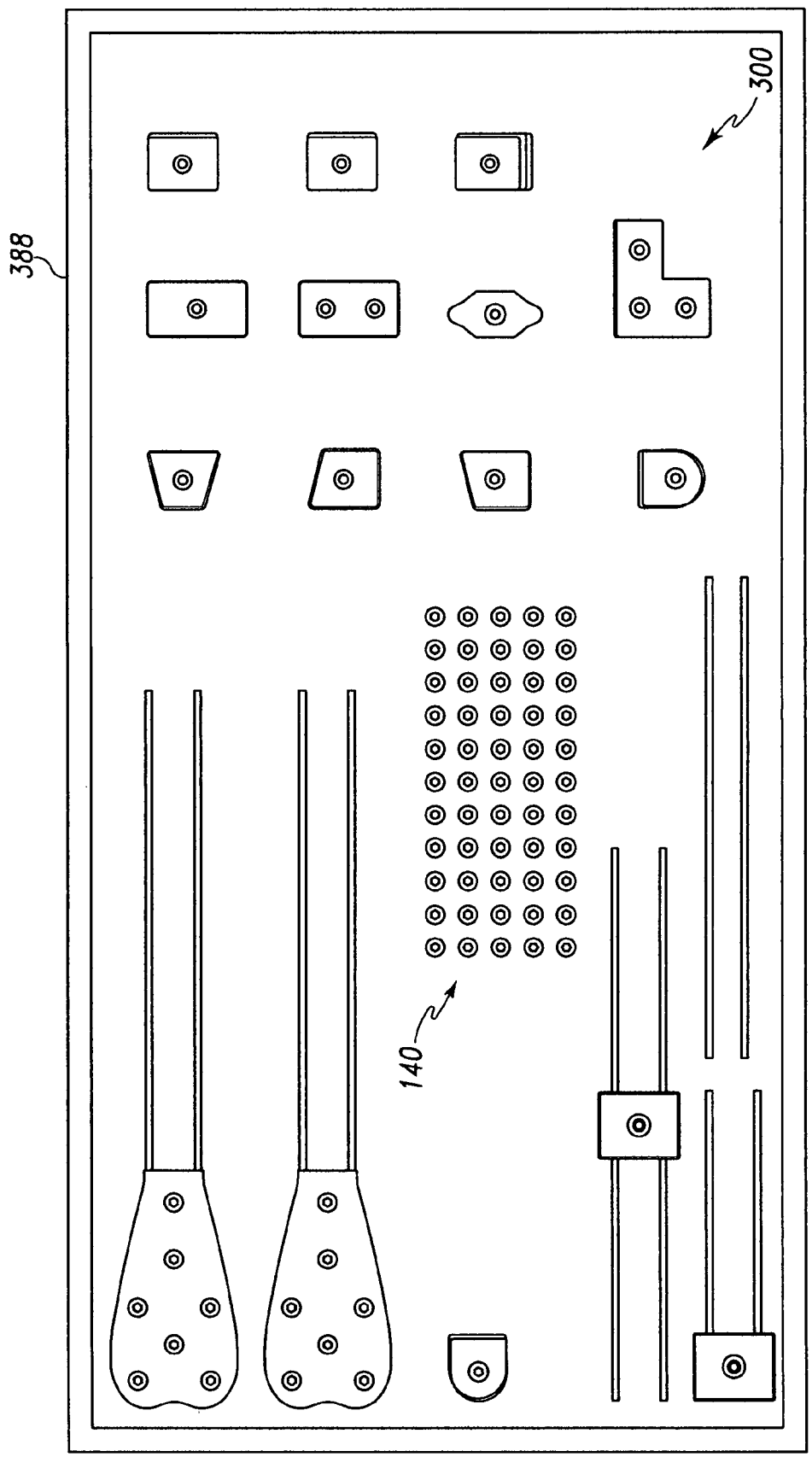
FIG. 25 is a top view of a kit including a sterilization tray containing several plate members that may be assembled into a plurality of alternate embodiments of a bone plate assembly such as the bone plate assembly shown in FIG. 18.

FIG. 25 shows a kit 301 including a tray 388 containing all the components that may be used for bone assembly 300. As for kits 201 and 301, kit 301 may be customized to provide the necessary components for specific types or classes of bone fracture repairs, and may be constructed of materials suitable for steam autoclave sterilization. The kit 301 may also include bone screws 140 for use with the plate members. It should be appreciated that the bone screws 140 may all be of the type of FIG. 6A and may be of varying lengths and sizes to accommodate different bones and different portions of bone. Further it should be appreciated that the bone screws may be of other types such as those shown in FIG. 16A.

Figure 26:
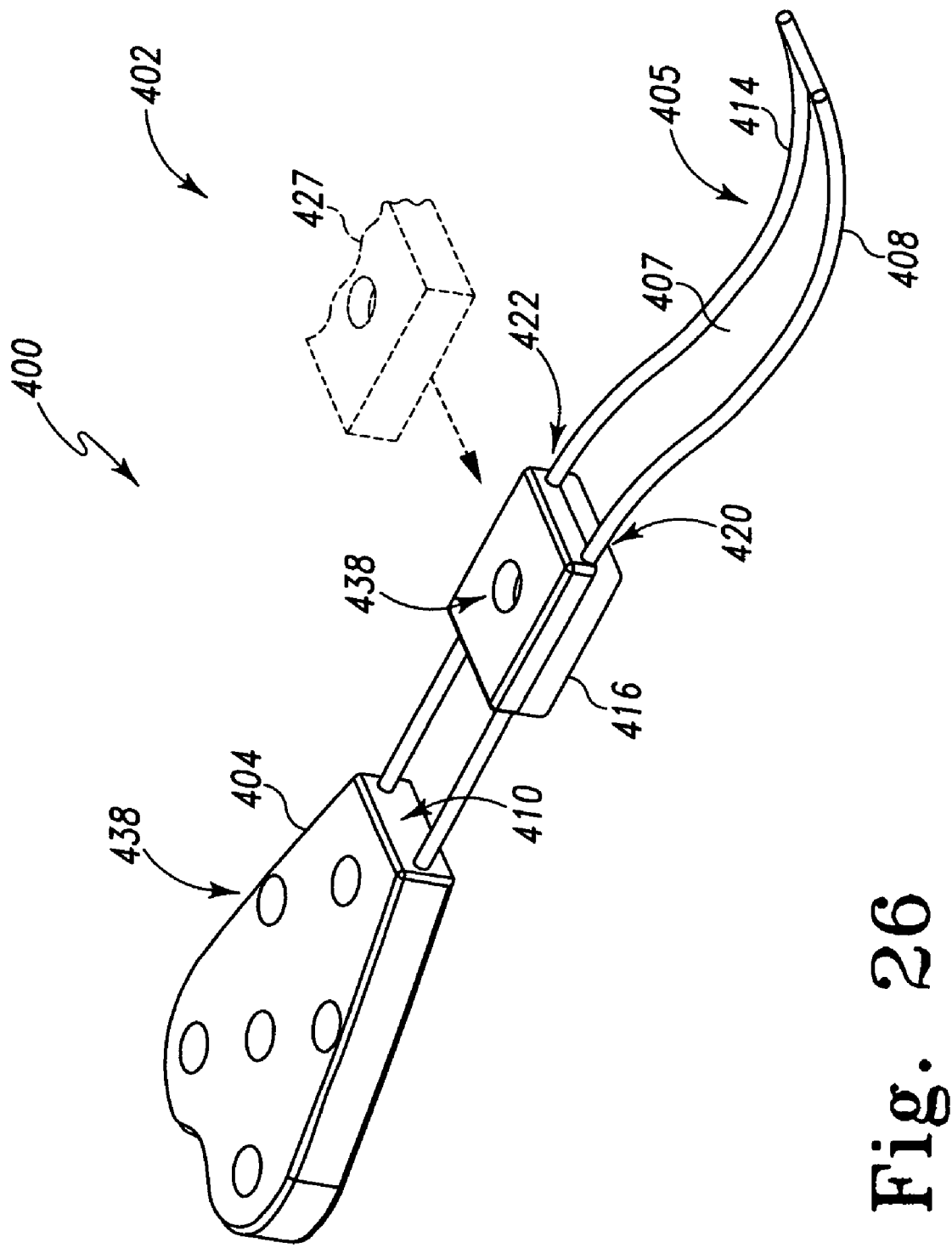
FIG. 26 is an isometric view of a bone plate assembly including a first plate member attached to a flexible track having a pair of spaced apart connectors, a second plate member fitted to the flexible track according to another embodiment of the present invention.

According to the present invention and referring now to FIG. 26 yet another embodiment is shown as bone plate assembly 400. The plate assembly 402 as shown in FIG. 26 includes a first plate member 404 to which a flexible track 405 is secured. The flexible track 405 extends outwardly from end 410 of the first plate member 404. The flexible track 405 includes a first connector 408 and a second spaced apart connector 414. The first connector 408 and the second connector 414 are contained by a webbed retainer 407. The webbed retainer 407 and the first connector 408 and second connector 414 form the flexible track 405.

The webbed retainer 407 may be formed from an implantable polymer that can withstand repeated cycles of a steam autoclave.

The webbed retainer 407 encapsulates the first connecting first connector 408 and the second connector 414. The retainer 407 may encapsulate the first connector 408 and the second connector 414 by, for example, an extruding process. Alternatively the first connector 408 and the second connector 414 may be heat-welded between layers of a polymeric film or between opposite sides of a flattened, thin wall, polymeric tube. Preferably, webbed retainer 407 loosely encapsulates connectors 408, 414 to permit sliding movement of the flexible members comprising each of the connectors, as in the previous embodiments, until clamped between the plate members. Also, webbed retainer 407 may be sufficiently thin, for example in the range of 0.1 to 0.5 mm, to allow a desired flexibility of flexible track 405 and to allow easy penetration by self-tapping bone screws when attached to the fractured bone. In addition, webbed retainer 407 may have a lubricious surface to facilitate assembly and adjustment of the plate members.

In addition to first plate member 404, the bone plate assembly 400 includes a second plate member 416 that is slidably fitted along the flexible track 405. The second plate member 406 includes a first channel 420 and a spaced apart second channel 422 which receive the first connector 408 and second connector 414 respectively. The second plate member 416 includes a transverse opening 438 for receiving bone screw 440.

Figure 27:
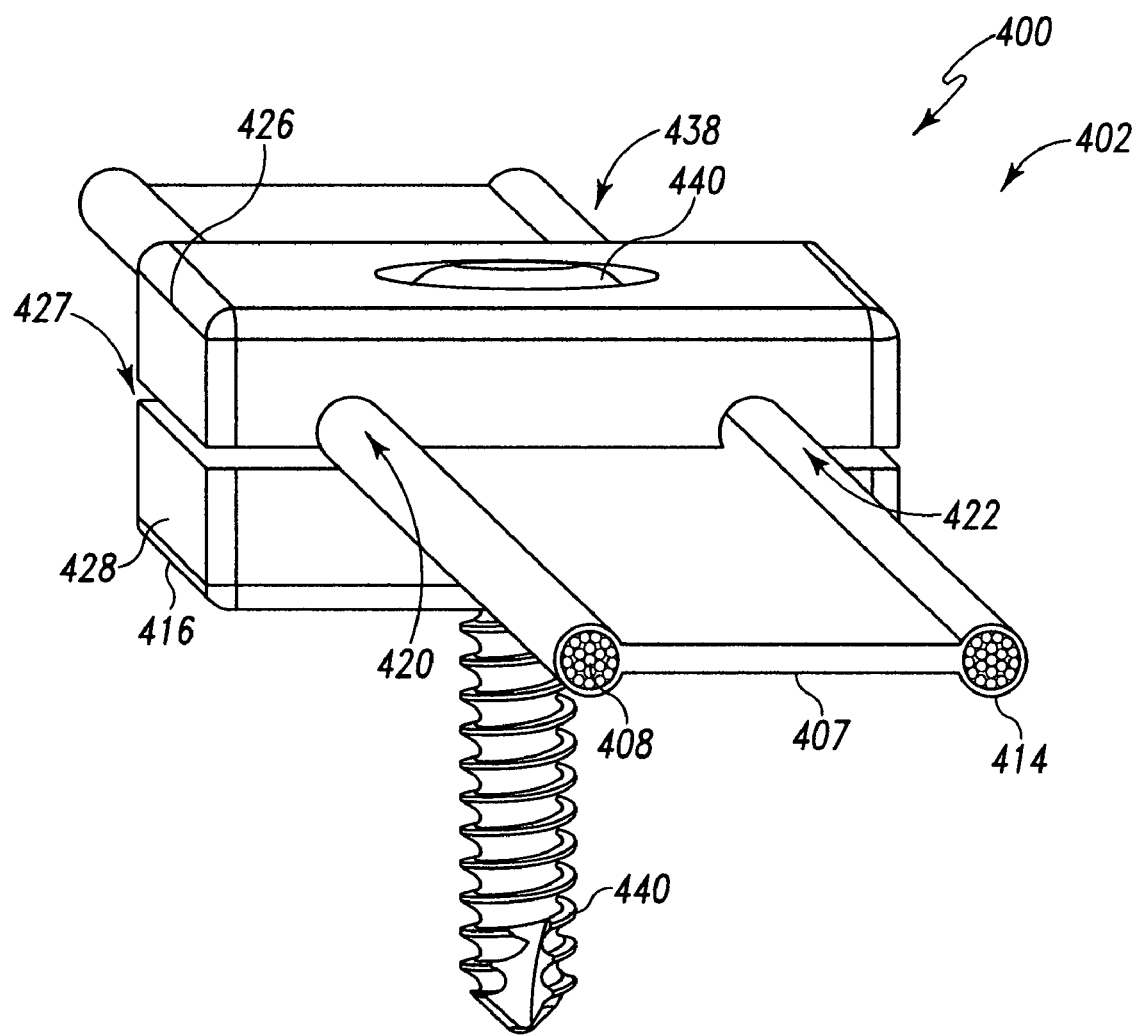
FIG. 27 is an isometric view of the second plate member of FIG. 26 showing a bone screw inserted through the second plate member and flexible track.
Figure 32:
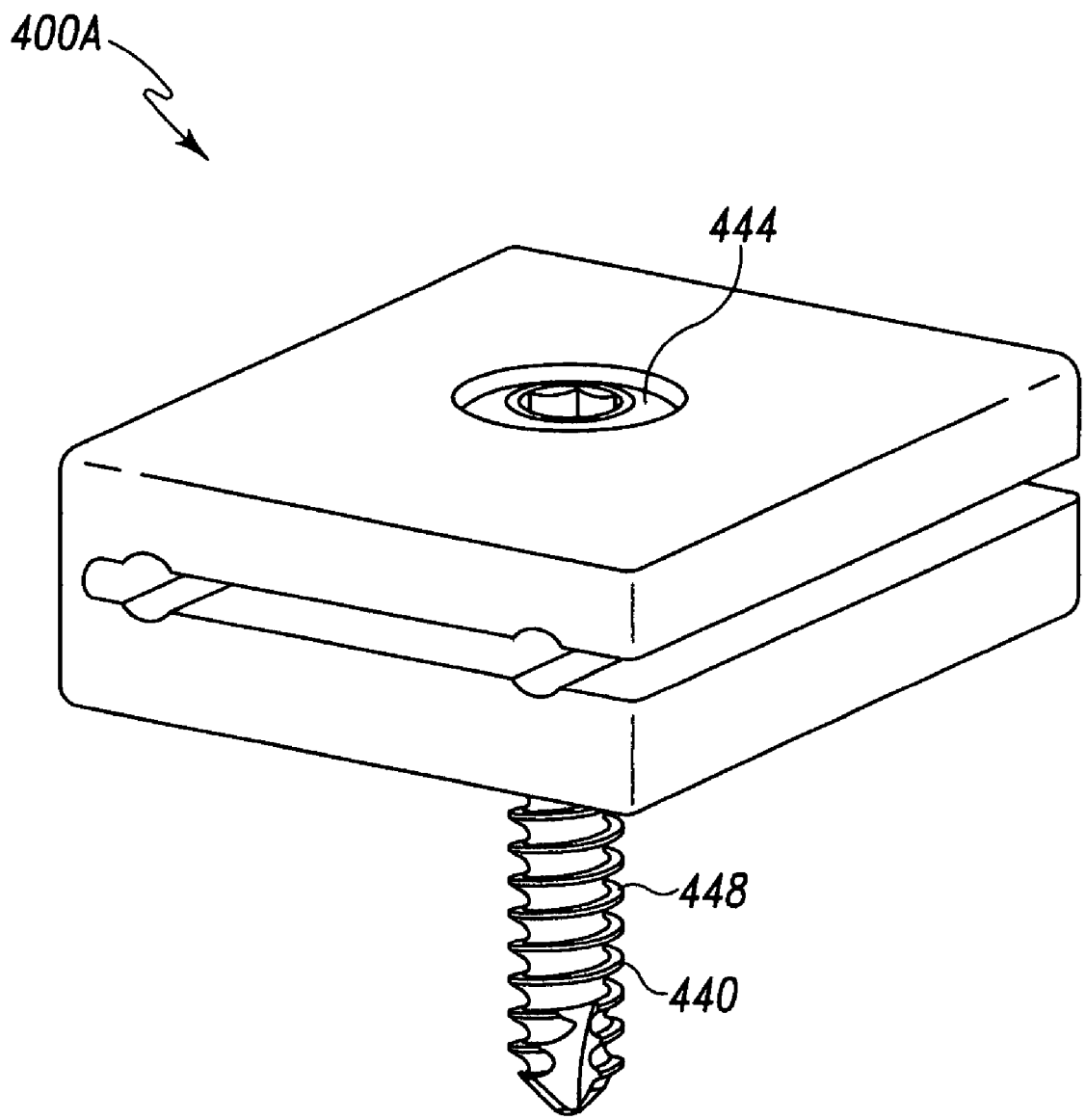
FIG. 32 is an isometric view of the second plate member of FIG. 29 including a fully inserted bone screw.

Referring now to FIG. 27, the second plate member 416 is shown in greater detail. The second plate member 416 includes an upper plate portion 426 and a second lower plate portion 428. The upper plate portion 426 and lower plate portion 428 define a gap 427 between each other. The gap between the upper plate portion 427 and the lower plate portion 428 may be accomplished by rivets, similar to those shown in FIGS. 2-6. Alternatively, as shown in FIG. 27, the upper plate portion 426 and lower plate portion 428 may be attached together by a bridge 429. As a consequence, plate member 416 may be assembled to the webbed flexible retainer member assembly in a "clip-on" fashion. FIG. 32 is an isometric view of plate member 416 with a bone screw fully inserted there through. It should be noted that the screw should not be inserted into plate member 416 while assembling to the flexible track 405.

For example and referring again to FIG. 26, the second plate member 416 may be installed in a direction generally transverse to the longitudinal axis of track 405, that is by advancing the plate member 416 from first position 427 as shown in phantom to second position 429 as shown in solid. By installing in this direction, the assembly of the plate members may be more readily performed particularly in less invasive procedures. In addition, it is not necessary to assemble the plate members in a proper sequence since each plate member can easily be positioned onto track 405 between other plate members already assembled to the track 405. Similarly, each assembled plate member may be removed from track 405 without requiring removal of adjacent plate members. It is possible, therefore, for the surgeon to easily modify the bone plate assembly 400 during the fracture repair procedure.

Figure 28:
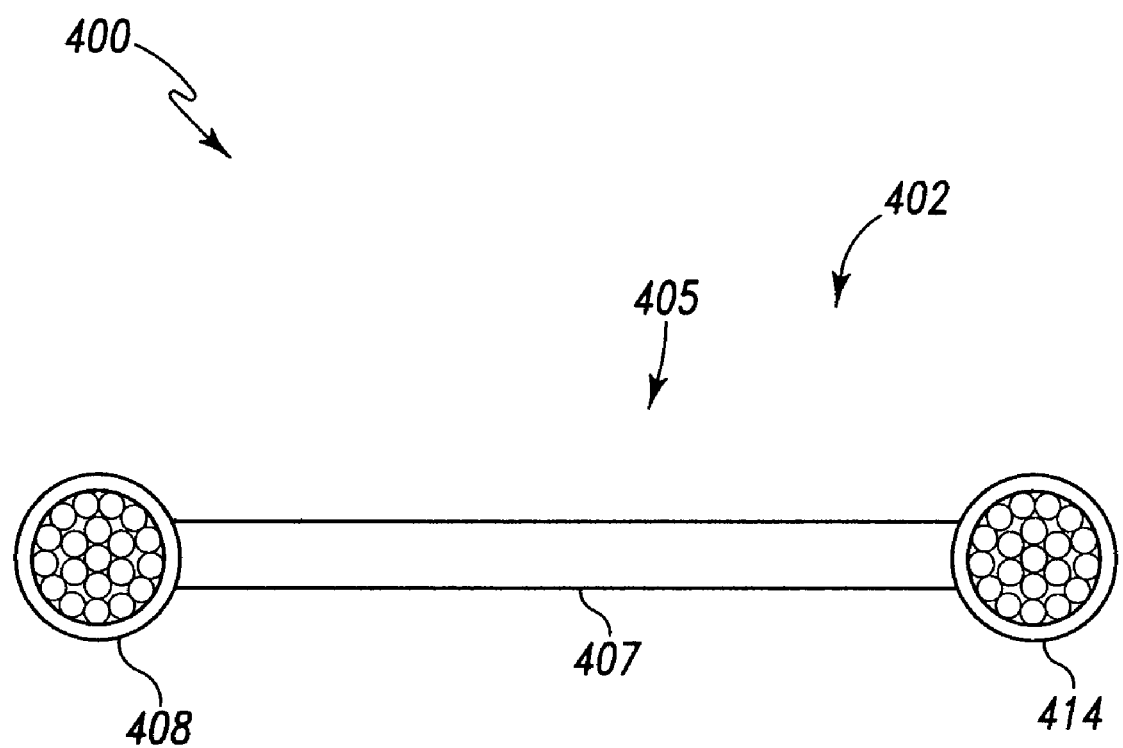
FIG. 28 is an end view of the flexible track of FIG. 27.

Referring now to FIG. 28 the flexible track 405 is shown in greater detail. As shown in FIG. 28 the first connector 408 and the second connector 414 are encapsulated by the retainer 407. As in previous embodiments, each of connectors 408 and 414 may include a grouping of a plurality of flexible members 409, 415 respectively, in any one of a number of possible arrangements. The flexible members may be formed, for example, from metallic wire or polymeric filaments and arranged in a circular grouping as shown in FIG. 28. Relative longitudinal movement among the flexible members permits flexibility of connectors 408, 414. When the plate members are tightly clamped around connectors 408, 414 to prohibit such relative longitudinal movement, the flexible track 405 becomes sufficiently rigid to provide fixation of the fractured bone.

Figure 29:
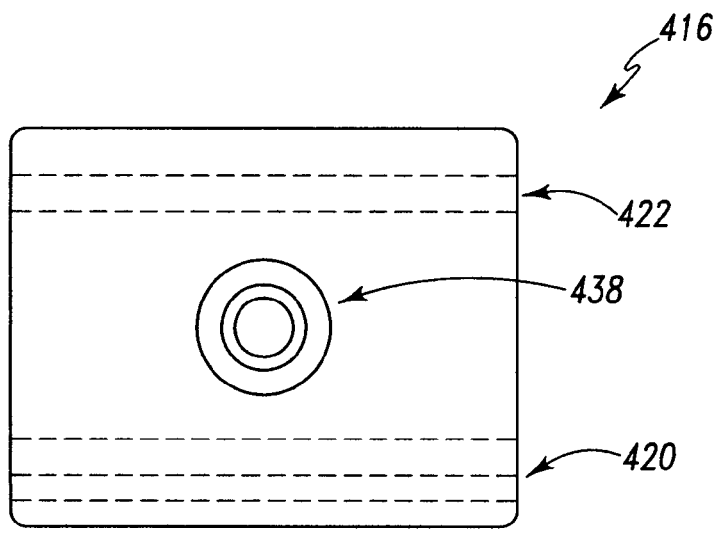
FIG. 29 is a top view of another embodiment of second plate member that may be assembled to the track of FIG. 28.
Figure 30:
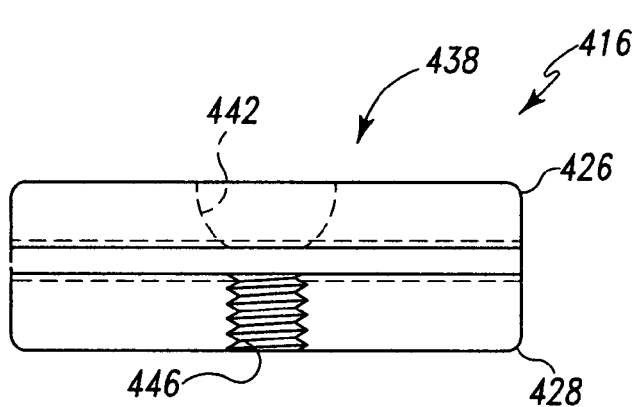
FIG. 30 is a side view of the second plate member of FIG. 29.
Figure 31:
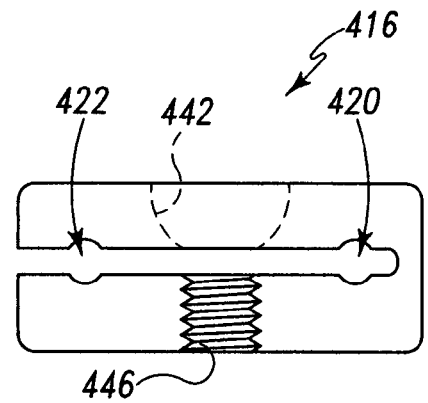
FIG. 31 is a end view of the second plate member of FIG. 29.
Figure 31A:
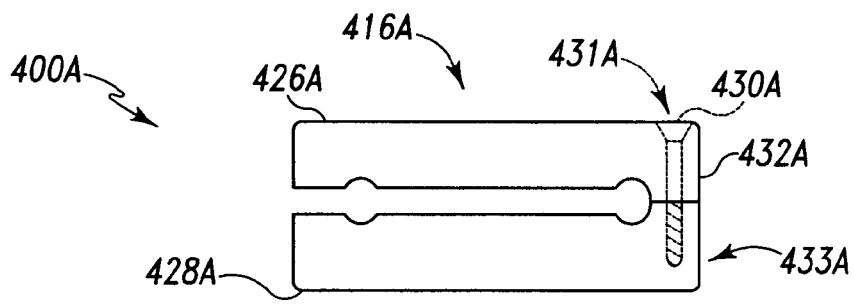
FIG. 31A is a end view of an alternate version of the second plate member shown in FIG. 31.

Referring now to FIGS. 29 through 31, the second plate member 416 is shown in greater detail. The second member 416 includes the first channel as well as the spaced apart second channel. An opening 438 is formed in the upper plate portion 426 and the lower plate portion 428 to permit the locking screw bone screw 440 to pass there through.

As shown in FIG. 30, internal threads 446 are formed in the opening 438. A counter bore 442 for receiving the head of the bone screw 440 is formed in upper plate portion 426 of the second plate member 416.

It is also possible to provide each plate member 416, as for all the previous embodiments of the plate member, without any threaded holes. It would then be necessary to tighten the bone screw until the plate member compresses tightly against the bone surface so that the plate member clamps onto the connectors with sufficient force to stiffen the bone plate assembly. This arrangement may be preferred in the repair of fractures in healthy bone but perhaps not in osteoporotic bone in which screw engagement in the weak bone tissue is not optimal.

A method for performing trauma surgery includes obtaining a 3D image of fractured bone, converting a 3D image into CAD model of fractured bone, inputting CAD model of the image into rapid prototype machine for example an SLA machine. The method 1100 further includes making a 3D physical model of the fractured bone, providing a bone fixation device, assembling the trial bone fixation device that conforms to a 3D physical model of the fractured bone and assembling the implantable bone fixation device having the same configuration as the trial device.

According to another aspect of the method of performing trauma surgery, the method includes providing a kit including a tray for storing a plurality of plate members and at least one connection member. At least two of the plate members have different shapes. The method further includes selecting at least one plate member from the plurality of plate members and at least one connection member from the plurality of connection members, assembling the selected at least one plate member to the selected one connecting member placing the assembled plate and connection member against the damaged bone and locking the plate to the connection member.

Although the present invention and its advantages have been described in detail, it should be understood that various changes, substitutions, and alterations can be made therein without departing from the spirit and scope of the present invention as defined by the appended claims.

We claim:

1. A kit for the construction of a bone plate assembly for fixation of a fractured bone, the kit comprising:
   a plurality of plate members;
   an elongated connecting member for retaining said plurality of plate members in a desired configuration; and
   a plurality of locking members for securing said plate members to the connecting member,
   wherein each of said plate members defines an elongated channel for receiving said connecting member therein, said channel defining a longitudinal axis,
   wherein each of said plurality of plate members defines a bone contacting surface, at least one transverse surface transverse to said longitudinal axis and configured for mutual planar contact between adjacent plate members, and a substantially planar side surface adjacent to the bone contacting surface and the at least one traverse surface; and
   wherein said transverse surface of at least one of the plurality of plate members is not perpendicular to said longitudinal axis so that when said transverse surface of said at least one plate member is in planar contact with said transverse surface of an adjacent plate member the longitudinal axes of the channels of the adjacent plate members are not coaxial.

2. The kit of claim 1 wherein;
   at least one of said locking members is a bone screw; and
   each plate member includes at least one opening for retaining said bone screw such that said bone screw may securely attach said plate member to the fractured bone.

3. The kit of claim 1 wherein said connecting member is flexible.

4. The kit of claim 1 wherein said connecting member securely retains said plurality of plate members in a first arrangement wherein each of said plurality of plate members is moveably orientable with respect to each other such that said bone plate assembly may generally conform to the surface of the fractured bone, and wherein said locking member may fixedly secure said plate members to said connecting member in a second arrangement such that said bone plate assembly is sufficiently rigid to provide fixation of the fractured bone.

5. The kit of claim 4 wherein said connecting member comprises a plurality of flexible members, and in the first arrangement the plurality of plate members are loosely retained on the connecting members such that the flexible members may move longitudinally relative to each other, and in the second arrangement plate members are clamped tightly onto the connecting members such that the flexible members are not permitted to move substantially relative to each other.

6. The kit of claim 1:
   wherein when retained by said plurality of plate members, said connecting member defines a longitudinal axis thereof through one of the elongated channels, a first dimension perpendicular to the bone contact surface and to the longitudinal axis thereof, and a second dimension parallel to the bone contact surface and normal to the longitudinal axis thereof, the first dimension being greater that the second dimension.

7. The kit of claim 6, wherein the first dimension is at least twice as large as the second dimension.

8. The kit of claim 1, wherein said plurality of plate members comprises
   a first plate member having a first bone contacting surface shape; and
   a second plate member having a second bone contacting surface shape, the second bone contacting surface shape being different from the first bone contacting surface shape.

9. The kit of claim 1, wherein said transverse surface of a first of the plurality of plate members and the transverse surface of a second of the plurality of plate members are mutually configured so that when said transverse surfaces are in contact the bone contacting surface of the first of the plurality of plate members and the bone contacting surface of the second of the plurality of plate members lie in different planes.

10. The kit of claim 1, further comprising a second connecting member for securing the plurality of plate members to each other, said second connecting member being spaced from said first mentioned connecting member when the first connecting member and the second connecting member are secured to the plurality of plate members.

11. The kit of claim 1, further comprising a tray for containing said plurality of plate members, said locking members and said connecting member prior to use.

12. A kit for forming an assembly for stabilizing a damaged bone, comprising:
   a first plate member having a first side adjacent to a first bone contacting surface and with a first connecting member extending therefrom, the first plate member defining a first channel configured to receive a second connecting member;
   a second plate member having a second side adjacent to a second bone contacting surface and with the second connecting member extending therefrom, said second plate member including a second channel configured to receive a third connecting member; and
   a third plate member having a third side adjacent to a third bone contacting surface and with the third connecting member extending therefrom, said third plate member including a third channel configured to receive the first connecting member, said second connecting member defining a first longitudinal axis, said second channel defining a second longitudinal axis, said second longitudinal axis being coplanar, non-parallel and non-coaxial with said first longitudinal axis.

13. The kit of claim 12, further comprising:
at least one locking member configured to secure the second plate member to the third connector when the third connector is received within the second channel, wherein the at least one locking member is a bone screw having bone engaging threads.

14. The kit of claim 1 wherein at least one of the plurality of plate members includes at least one arcuate surface opposite said transverse surface and adjacent to said bone contacting surface.

15. The kit of claim 1, wherein:
said transverse surface of said at least one plate member is not perpendicular to said bone contacting surface.

16. The kit of claim 13, wherein the second plate member is configured to receive the bone screw such that when the bone screw is received by the second plate member, the bone screw can be used to compress the second plate member such that when the third connector is received within the second channel, the second plate member is secured to the third connector.

17. The kit of claim 12, wherein:
the first plate member includes a fourth connecting member extending from the first side, and defines a fourth channel parallel to the first channel and configured to receive a fifth connecting member;
the second plate member includes the fifth connecting member extending from the second side, and defines a fifth channel parallel to the second channel and configured to receive a sixth connecting member; and
the third plate member includes the sixth connecting member extending from the third side, and defines a sixth channel parallel to the third channel and configured to receive the fourth connecting member.

* * * * *